(12) United States Patent
Linder et al.

(10) Patent No.: US 8,389,272 B2
(45) Date of Patent: *Mar. 5, 2013

(54) FLUID DELIVERY SYSTEM AND METHOD

(75) Inventors: Vincent Linder, Watertown, MA (US); Samuel K. Sia, New York, NY (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/226,154

(22) Filed: Sep. 6, 2011

(65) Prior Publication Data

US 2011/0315229 A1 Dec. 29, 2011

Related U.S. Application Data

(63) Continuation of application No. 10/587,156, filed as application No. PCT/US2005/003514 on Jan. 26, 2005, now Pat. No. 8,030,057.

(60) Provisional application No. 60/539,358, filed on Jan. 26, 2004, provisional application No. 60/539,416, filed on Jan. 26, 2004, provisional application No. 60/565,866, filed on Apr. 26, 2004.

(51) Int. Cl.
*C12M 1/34* (2006.01)

(52) U.S. Cl. .................. 435/286.4; 435/288.5; 422/81; 422/82; 222/61; 222/72

(58) Field of Classification Search ................ None
See application file for complete search history.

(56) References Cited

U.S. PATENT DOCUMENTS

| | | |
|---|---|---|
| 3,735,640 A | 5/1973 | Chizhov et al. |
| 4,318,994 A | 3/1982 | Meyer et al. |
| 4,517,302 A | 5/1985 | Saros |
| 4,963,498 A | 10/1990 | Hillman et al. |
| 5,051,237 A | 9/1991 | Grenner et al. |
| 5,219,762 A | 6/1993 | Katamine et al. |
| 5,268,147 A | 12/1993 | Zabetakis et al. |
| 5,286,454 A | 2/1994 | Nilsson et al. |
| 5,376,252 A | 12/1994 | Ekström et al. |
| 5,478,751 A | 12/1995 | Oosta et al. |
| 5,486,335 A | 1/1996 | Wilding et al. |
| 5,571,410 A | 11/1996 | Swedberg et al. |
| 5,635,358 A | 6/1997 | Wilding et al. |
| 5,637,469 A | 6/1997 | Wilding et al. |
| 5,726,026 A | 3/1998 | Wilding et al. |
| 5,731,212 A | 3/1998 | Gavin et al. |
| 5,783,148 A | 7/1998 | Cottingham et al. |
| 5,866,345 A | 2/1999 | Wilding et al. |
| 5,876,675 A | 3/1999 | Kennedy |
| 5,942,443 A | 8/1999 | Parce et al. |

(Continued)

FOREIGN PATENT DOCUMENTS

| | | |
|---|---|---|
| EP | 0 110 771 B1 | 3/1988 |
| EP | 0 281 201 | 9/1988 |

(Continued)

OTHER PUBLICATIONS

Ahn, C. et al., "Disposable Smart Lab on a Chip for Point-of-Care Clinical Diagnostics", Proceedings of the IEEE, vol. 92, No. 1, pp. 154-173 (2004).

(Continued)

*Primary Examiner* — N. C. Yang
(74) *Attorney, Agent, or Firm* — Wolf, Greenfield & Sacks, P.C.

(57) ABSTRACT

A method and apparatus for delivering one or more fluids. Fluids may be delivered sequentially from a common vessel to a chemical, biological or biochemical process.

48 Claims, 12 Drawing Sheets

U.S. PATENT DOCUMENTS

| | | | |
|---|---|---|---|
| 5,955,028 | A | 9/1999 | Chow |
| 5,957,579 | A | 9/1999 | Kopf-Sill et al. |
| 6,019,944 | A | 2/2000 | Buechler |
| 6,042,709 | A | 3/2000 | Parce et al. |
| 6,046,056 | A | 4/2000 | Parce et al. |
| 6,103,199 | A | 8/2000 | Bjornson et al. |
| 6,136,272 | A | 10/2000 | Weigl et al. |
| 6,146,489 | A | 11/2000 | Wirth |
| 6,146,589 | A | 11/2000 | Chandler |
| 6,168,948 | B1 | 1/2001 | Anderson et al. |
| 6,176,962 | B1 | 1/2001 | Soane et al. |
| 6,184,029 | B1 | 2/2001 | Wilding et al. |
| 6,186,660 | B1 | 2/2001 | Kopf-Sill et al. |
| 6,214,560 | B1 | 4/2001 | Yguerabide et al. |
| 6,238,538 | B1 | 5/2001 | Parce et al. |
| 6,241,560 | B1 | 6/2001 | Furusawa et al. |
| 6,251,343 | B1 | 6/2001 | Dubrow et al. |
| 6,274,337 | B1 | 8/2001 | Parce et al. |
| 6,296,020 | B1 | 10/2001 | McNeely et al. |
| 6,331,439 | B1 | 12/2001 | Cherukuri et al. |
| 6,333,200 | B1 | 12/2001 | Kaler et al. |
| 6,361,958 | B1 | 3/2002 | Shieh et al. |
| 6,413,782 | B1 | 7/2002 | Parce et al. |
| 6,416,642 | B1 | 7/2002 | Alajoki et al. |
| 6,429,025 | B1 | 8/2002 | Parce et al. |
| 6,432,720 | B2 | 8/2002 | Chow |
| 6,479,299 | B1 | 11/2002 | Parce et al. |
| 6,488,872 | B1 | 12/2002 | Beebe et al. |
| 6,488,894 | B1 | 12/2002 | Miethe et al. |
| 6,488,896 | B2 | 12/2002 | Weigl et al. |
| 6,551,841 | B1 | 4/2003 | Wilding et al. |
| 6,610,499 | B1 | 8/2003 | Fulwyler et al. |
| 6,613,512 | B1 | 9/2003 | Kopf-Sill et al. |
| 6,613,525 | B2 | 9/2003 | Nelson et al. |
| 6,620,625 | B2 | 9/2003 | Wolk et al. |
| 6,632,619 | B1 | 10/2003 | Harrison et al. |
| 6,638,482 | B1 | 10/2003 | Ackley et al. |
| 6,656,430 | B2 | 12/2003 | Sheppard, Jr. et al. |
| 6,669,831 | B2 | 12/2003 | Chow et al. |
| 6,705,357 | B2 | 3/2004 | Jeon et al. |
| 6,709,869 | B2 | 3/2004 | Mian et al. |
| 6,716,620 | B2 | 4/2004 | Bashir et al. |
| 6,742,661 | B1 | 6/2004 | Schulte et al. |
| 6,761,962 | B2 | 7/2004 | Bentsen et al. |
| 6,780,584 | B1 | 8/2004 | Edman et al. |
| 6,794,197 | B1 | 9/2004 | Indermuhle et al. |
| 6,818,184 | B2 | 11/2004 | Fulwyler et al. |
| 6,827,095 | B2 | 12/2004 | O'Connor et al. |
| 6,828,143 | B1 | 12/2004 | Bard |
| 6,830,936 | B2 | 12/2004 | Anderson et al. |
| 6,858,185 | B1 | 2/2005 | Kopf-Sill et al. |
| 6,878,271 | B2 | 4/2005 | Gilbert et al. |
| 6,878,755 | B2 | 4/2005 | Singh et al. |
| 6,949,377 | B2 | 9/2005 | Ho |
| 6,953,550 | B2 | 10/2005 | Sheppard, Jr. et al. |
| 6,989,128 | B2 | 1/2006 | Alajoki et al. |
| 7,005,292 | B2 | 2/2006 | Wilding et al. |
| 7,015,046 | B2 | 3/2006 | Wohlstadter et al. |
| 7,018,830 | B2 | 3/2006 | Wilding et al. |
| 7,067,263 | B2 | 6/2006 | Parce et al. |
| 7,087,148 | B1 | 8/2006 | Blackburn et al. |
| 7,091,048 | B2 | 8/2006 | Parce et al. |
| 8,030,057 | B2 * | 10/2011 | Linder et al. ............... 435/286.4 |
| 2002/0001818 | A1 | 1/2002 | Brock |
| 2002/0019059 | A1 | 2/2002 | Chow et al. |
| 2002/0071788 | A1 | 6/2002 | Fujii et al. |
| 2002/0092767 | A1 | 7/2002 | Bjornson et al. |
| 2002/0142618 | A1 | 10/2002 | Parce et al. |
| 2002/0199094 | A1 | 12/2002 | Strand et al. |
| 2003/0012697 | A1 | 1/2003 | Hahn et al. |
| 2003/0082081 | A1 | 5/2003 | Fouillet et al. |
| 2003/0118486 | A1 | 6/2003 | Zhou et al. |
| 2003/0124623 | A1 | 7/2003 | Yager et al. |
| 2003/0138969 | A1 | 7/2003 | Jakobsen et al. |
| 2003/0185713 | A1 | 10/2003 | Leonard et al. |
| 2003/0207328 | A1 | 11/2003 | Yguerabide et al. |
| 2004/0077074 | A1 | 4/2004 | Ackley et al. |
| 2004/0115094 | A1 | 6/2004 | Gumbrecht et al. |
| 2004/0228771 | A1 | 11/2004 | Zhou et al. |
| 2005/0118073 | A1 | 6/2005 | Facer et al. |
| 2005/0161669 | A1 | 7/2005 | Jovanovich et al. |
| 2005/0221281 | A1 | 10/2005 | Ho |
| 2005/0238545 | A1 | 10/2005 | Parce et al. |
| 2005/0255003 | A1 | 11/2005 | Summersgill et al. |
| 2006/0002827 | A1 | 1/2006 | Curcio et al. |
| 2006/0094119 | A1 | 5/2006 | Ismagilov et al. |
| 2006/0257992 | A1 | 11/2006 | McDevitt et al. |
| 2006/0275852 | A1 | 12/2006 | Montagu |
| 2007/0048189 | A1 | 3/2007 | Cox et al. |
| 2007/0298433 | A1 | 12/2007 | Sia et al. |
| 2008/0085219 | A1 | 4/2008 | Beebe et al. |
| 2008/0248590 | A1 | 10/2008 | Gulliksen et al. |

FOREIGN PATENT DOCUMENTS

| | | |
|---|---|---|
| EP | 0 430 248 | 6/1991 |
| EP | 0 643 307 A1 | 3/1995 |
| EP | 1 054 259 A1 | 11/2000 |
| EP | 1946830 A1 | 7/2008 |
| EP | 2071026 A1 | 6/2009 |
| WO | WO 91/01003 A | 1/1991 |
| WO | WO 02/22250 A2 | 3/2002 |
| WO | WO 03/054513 A2 | 7/2003 |
| WO | WO 2004/087951 A2 | 10/2004 |
| WO | WO 2004/087951 A3 | 10/2004 |
| WO | WO 2005/056186 A1 | 6/2005 |
| WO | WO 2005/072858 | 8/2005 |
| WO | WO 2006/018044 A1 | 2/2006 |
| WO | WO 2006/056787 A1 | 6/2006 |
| WO | WO 2006/113727 A2 | 10/2006 |
| WO | WO 2008/118098 A1 | 10/2008 |
| WO | WO 2008/123112 A1 | 10/2008 |

OTHER PUBLICATIONS

Andersson, et al., "Micromachined flow-through filter-chamber for chemical reactions on beads", Sensors and Actuators, vol. B67, pp. 203-208 (2000).

Atencia, J., et al., "Capillary inserts in microcirculatory systems," Lab on a Chip, vol. 6, pp. 575-577 (2006).

Atencia, J., et al., "Steady flow generation in microcirculatory systems," Lab on a Chip, vol. 6, pp. 567-574 (2006).

Dardion, et al., "Chemical sensing using an integrated microfluidic system based on the Berthelot reaction", Sensors and Actuators B, vol. 76, pp. 235-243 (2001).

Dodge, et al., "Electrokinetically Driven Microfluidic Chips with Surface-Modified Chambers for Heterogeneous Immunoassays", Anal. Chem., vol. 73, pp. 3400-3409 (2001).

Fredrickson, C., et al., "Macro-to-micro interfaces for microfluidic devices," Lab on a Chip, vol. 4, pp. 526-533 (2004).

Grodzinski, P. et al., "A Modular Microfluidic System for Cell Pre-concentration and Genetic Sample Preparation", Biomedical Microdevices, 5:4,303-310 (2003).

International Search Report and Written Opinion for PCT/US2008/005577 mailed Apr. 3, 2009.

International Search Report and Written Opinion for PCT/US2008/010022, mailed May 6, 2009.

International Search Report dated May 13, 2005 in PCT/US2005/003514.

Invitation to Pay Additional Fees and International Communication of the Partial International Search for International Application No. PCT/US2009/006596, mailed Apr. 19, 2010.

Juncker, et al., "Autonomous Microfluidic Capillary Systems", Anal. Chem, vol. 74, pp. 6139-6144 (2002).

Linder, et al., "Reagent-Loaded Cartridges for Valveless and Automated Fluid Delivery in Microfluidic Devices," *Anal Chem.*, vol. 77, No. 1, pp. 64-71 (2005).

Moorthy, et al., "Microfluidic tectonics platform: A colorimetric, disposable botulinum toxin enzyme-linked immunosorbent assay system", Electrophoresis, vol. 25, pp. 1705-1713 (2004).

Obeid et al., "Microfabricated device for DNA and RNA amplification by continuous-flow polymerase chain reaction and reverse transcription-polymerase chain reaction with cycle number selection", *Anal. Chem.*, vol. 75, (2003) 288-295.

Proceedings of uTAS 2004, 8th International Conference on Miniaturized Systems in Chemistry and Life Sciences, Sep. 26-30, Malmo, Sweden, Edited by Thomas Laurell, Johan Nilsson, Klavs Jensen, D. Jed Harrison, Jorg P. Kutter, The Royal Society of Chemistry, pp. 1-135 (2004).

Sia, S., et al., "An Integrated Approach to a Portable and Low-Cost Immunoassay for Resource-Poor Settings", Angew. Chem. Int. Ed., vol. 43, pp. 498-502 (2004).

Sia, S., et al., "Microfluidic devices fabricated in poly(dimethlysiloxane) for biological studies", Electrophoresis, vol. 24, pp. 3563-3576 (2003).

Song et al., "A microfluidic system for controlling reaction networks in time", *Angew. Chem. Int. Ed.*, vol. 42, No. 7, (2003) 767-772.

Weigle, et al., "Lab-on-a-chip for drug development", Advanced Drug Delivery Reviews, vol. 55, pp. 349-377 (2003).

Written Opinion dated May 13, 2005 in PCT/US2005/003514.

\* cited by examiner

FLUID DELIVERY SYSTEM AND METHOD

RELATED APPLICATIONS

This application is a continuation of U.S. application Ser. No. 10/587,156, filed May 16, 2007, which is a U.S. National Application of International Application No. PCT/US2005/003514, filed Jan. 26, 2005, which claims benefit under 35 U.S.C. §119(e) of U.S. Provisional Application Ser. No. 60/539,358, filed Jan. 26, 2004, U.S. Provisional Application Ser. No. 60/539,416, filed Jan. 26, 2004 and U.S. Provisional Application Ser. No. 60/565,866, filed Apr. 26, 2004, all of which are which are incorporated herein by reference.

GOVERNMENT FUNDING

This invention was made with government support under GM051559 awarded by National Institutes of Health and under ECS-0004030 awarded by National Science Foundation. The government has certain rights in the invention.

BACKGROUND OF INVENTION

1. Field of Invention

This invention relates to a method and apparatus for the delivery and/or storage of one or more fluids and, in particular, to a method and apparatus for storing and delivering chemical and biological reagents.

2. Discussion of Related Art

The delivery of fluids plays an important role in fields such as chemistry, microbiology and biochemistry. These fluids may include liquids or gases and may provide reagents, solvents, reactants, or rinses to chemical or biological processes. Often, more than one fluid is delivered to a reaction vessel or site to promote interaction between the fluids or components of the fluids. Intermittent rinse fluids may also be used to remove unwanted reactants or to prepare a reactor, reaction site or assay site.

While various microfluidic devices and methods, such as microfluidic assays, can provide inexpensive, sensitive and accurate analytical platforms, fluid delivery to the platform can add a level of cost and sophistication that may require testing to be performed in a laboratory rather than in the field, where it may be most useful.

As chemical and biochemical platforms become smaller due to improvements in areas such as microfluidics, smaller reagent quantities are required to do a similar number of assays or reactions. Typically, however, smaller size platforms do not diminish the need to supply multiple reagents and rinses to a reaction site. For instance, some microfluidic assays may require less than a microliter of reagent fluids, but two, three or more different fluids may need to be supplied in accurate quantities and in proper sequence.

For microfluidic assays and reactors, fluids are often supplied by an operator using a micropipette. A fluid may be pipetted into an inlet of a microfluidic system and the fluid may be drawn through the system by application of a vacuum source to the outlet end of the microfluidic system. Reagents may also be pumped in, for instance by using different syringe pumps filled with the required reagents. After one fluid is pumped into the microfluidic device, a second can be pumped in by disconnecting a line from the first pump and connecting a line from a second pump. Alternatively, valving may be used to switch from one pumped fluid to another. Different pumps are used for each fluid to avoid cross contamination. This may be of particular relevance when two fluids contain components that may react with each other or, when mixed, can affect the results of an assay or reaction.

Continuous flow systems may use a series of two different fluids passing serially through a reaction channel. Fluids can be pumped into a channel in serial fashion by switching, through valving, the fluid source that is feeding the tube. The fluids constantly move through the system in sequence and are allowed to react in the channel. For example, a PCR reaction can be run using continuous flow. See Obeid et al., "Microfabrication Device for DNA and RNA Amplification by Continuous-Flow Polymerase Chain Reaction and Reverse Transcription-Polymerase Chain Reaction with Cycle Number Selection," *Analytical Chemistry*, 2003, 75, 288-295.

The utility of fluid systems may be affected by the storage time, or shelf life, of any reagents that are to be used with a system. A portable microfluidic system can be transported to almost any location, but when reagents must be freshly prepared, the usefulness of the system in the field can be diminished. This may be true in particular for biological and biochemical based systems that may rely on reagents that, for example, are unstable, have short shelf lives or must be stored under special conditions, such as refrigeration.

An accurate early and ongoing determination of a disease condition is important for the prevention and treatment of human and animal diseases. One class of diagnostic techniques uses immunoassay reactions to detect the presence of either an antigen or an antibody in a sample taken from a subject. These immunoassay methods include, for example, ELISA, immunochromatographic assays (strip tests, dipstick assays and lateral flow assays), and sandwich assays. Accuracy, reliability, and ease of use of these types of assays has improved, but often testing requires laboratory conditions, power supplies, and training that may not be available in some areas where testing is desired.

One type of sandwich assay uses gold conjugated antibodies to enhance detection. For example, see PCT publication WO/91/01003. Enhancement of a gold colloid signal can be achieved by staining the gold colloids with silver. First, an antigen is immobilized onto a solid polystyrene substrate. A human anti-HIV antibody is then captured by the antigen and is therefore itself immobilized on the substrate. The antibody is then exposed to anti-human IgG labeled with a colloidal gold particle and thus labeled IgG becomes bonded to the antibody. The antigen-antibody-IgG complex is then exposed to a solution containing silver ions and these become nucleated around the gold particles as solid silver particles having a dark color to the eye.

The development of microfluidics and microfluidic techniques has provided improved chemical and biological research tools, including platforms for performing chemical reactions, combining and separating fluids, diluting samples, and generating gradients. For example, see U.S. Pat. No. 6,645,432, hereby incorporated by reference herein.

SUMMARY OF INVENTION

In one aspect, the invention is a method, the method comprising providing a first and a second fluid maintained separately from each other in a common vessel, transferring the first and second fluids in series from the vessel to a reaction site to carry out a predetermined chemical or biochemical reaction, and avoiding contact between the first and second fluids, at least until after the fluids have been applied to the reaction site.

In another aspect, an apparatus is provided, the apparatus comprising a sealed vessel, a first static fluid disposed in the vessel, a second static fluid disposed in the vessel, and a third static fluid disposed in the vessel, wherein the third fluid separates the first and second fluids, and at least the first and second fluids are selected for use in a predetermined chemical or biological reaction in a predetermined sequence.

In another aspect, another method is provided, the method comprising flowing a first fluid into a vessel, flowing a second fluid into the vessel, the second fluid being substantially immiscible with the first fluid, flowing a third fluid into the vessel, wherein the third fluid is substantially immiscible with the second fluid and wherein the third fluid is not contacting the first fluid, and sealing the fluids in the vessel.

In another aspect another apparatus is provided, the apparatus comprising a sealed vessel comprising a chamber, defining a continuous void, containing a first fluid and a second fluid, the first and second fluids constructed and arranged to be deliverable from the vessel separately for sequential use in a predetermined chemical or biological reaction wherein the sealed vessel is constructed and arranged for storing the first and second fluids for at least one hour prior to use of the first and second fluids in the predetermined chemical or biological reaction.

In another aspect an assay kit is provided, the kit comprising a surface including a microfluidic channel, at least one of an antibody or an antigen associated with a portion of the microfluidic channel, a vessel, a first static fluid disposed in the vessel, the first static fluid comprising a metal colloid associated with an antibody or an antigen, a second static fluid disposed in the vessel, the second static fluid comprising a metal precursor, a third static fluid disposed in the vessel wherein the third fluid separates the first and second fluids, and instructions for performing the assay.

In another aspect, another method is provided, the method comprising providing a first and a second fluid statically maintained separately from each other in a common vessel for greater than one minute, applying in series the first and second fluid to a reaction site, and avoiding contact between the first and second fluids, at least until after the fluids have been applied to the reaction site.

In another aspect a method is provided, the method comprising providing a first and a second fluid maintained separately from each other in a common vessel, transferring the first and second fluids in series from the vessel to a reaction site to carry out a predetermined chemical or biochemical reaction, allowing a component of the first fluid to become associated with the reaction site, and allowing a component of the second fluid to become associated with the component of the first fluid.

BRIEF DESCRIPTION OF DRAWINGS

The accompanying drawings, are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
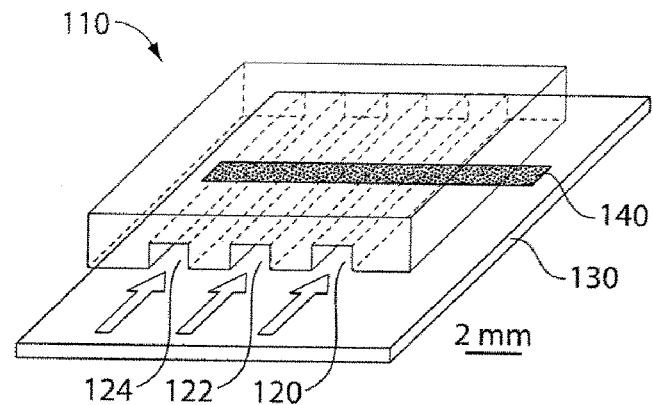
FIG. 1 is an illustration of one embodiment of an assay of the invention.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

The invention relates to a method and apparatus for the delivery of fluids. The term "fluid" is used herein, as it is commonly by those skilled in the art, to include both liquids and gases, including gaseous mixtures. Also included are aqueous and non-aqueous solvents, solutions and suspensions.

A "reaction site" is a location where a chemical, physical or biochemical process occurs. These processes may include any of, for example, chemical reactions, electrochemical photochemical reactions, chemical and biological assays such as disease condition assessment, immunoassays, nucleic acid binding and/or identification, and protein binding and/or identification. Also included are finishing processes, surface treatments and phase-altering reactions.

As used herein, "immiscible" is used according to its common meaning in the art. Specifically, a first fluid is immiscible in a second fluid if the first fluid is not substantially soluble in the second fluid. In some instances, a first fluid may be immiscible in a second fluid if it is less than 0.1%, less than 1%, less than 10% or less than 50% soluble in a second fluid under environmental conditions at which the fluids are stored or used.

"Integral article" means a single piece of material, or assembly of components integrally connected with each other. As used herein, the term "integrally connected," when referring to two or more objects, means objects that do not become separated from each other during the course of normal use, e.g., cannot be separated manually; separation requires at least the use of tools, and/or by causing damage to at least one of the components, for example, by breaking, peeling, etc. (separating components fastened together via adhesives, tools, etc.).

"Instructions" can and often do define a component of promotion, and typically involve written instructions on or associated with packaging of compositions of the invention, optionally as part of a kit. Instructions also can include any oral or electronic instructions provided in any manner. The "kit" typically, and preferably defines a package including both any one or a combination of the components or devices of the invention and the instructions, but can also include components or devices of the invention and instructions of any form that are provided in connection with the components or devices in a manner such that a clinical professional will clearly recognize that the instructions are to be associated with the components or devices.

In some, but not all embodiments, all or some of the components of the systems and methods described herein are microfluidic. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria.

The "cross-sectional dimension" of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g. an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

A "plug" is defined herein as a continuous volume of a first fluid, the boundaries of which are defined by a wall or walls of a vessel and one or more interfaces with a second fluid that is substantially immiscible with the first fluid. An example of a plug would be a one microliter volume of an aqueous solution in a capillary tube bounded by air at both ends of the one microliter volume. Another example of a plug would be a one milliliter volume of a non-aqueous liquid in a sealed length of tubing, the non-aqueous fluid being bounded at one end by the sealed end of the tubing and at the opposing end by an aqueous liquid.

If a fluid is "statically maintained" in a vessel, the fluid does not change its position in relation to the vessel although it may, for example, expand or contract or vibrate in its statically maintained position. The vessel containing the fluid may be moved or re-oriented while the fluid is statically maintained.

If a fluid is of the same "type" as a second fluid, it means that the two fluids serve the same purpose in an assay or reaction, although they may be of different volumes. For example, two different rinse solutions would be considered the same type of solution while a solution including a reagent would not be of the same type as a rinse solution.

If two fluids are "distinct" from each other, they are not intermixed and fill separately distinguishable volumes. For instance, two fluids may be distinct if they are immiscible or if they are physically separated, such as by a separation fluid.

The term "binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

An "opaque material" is a substance that interferes with the transmittance of light at one or more wavelengths. An opaque material does not merely refract light, but reduces the amount of transmission through the material by, for example, absorbing or reflecting light. Different opaque materials or different amounts of an opaque material may allow transmittance of less than 90, 80, 70, 60, 50, 40, 30, 20, 10 or 1 percent of the light illuminating the opaque material. Examples of opaque materials include molecular layers of elemental metal and polymeric layers.

The term "binding partner" refers to a molecule that can undergo binding with a particular molecule. Biological binding partners are examples. For instance, Protein A is a binding partner of the biological molecule IgG, and vice versa. Likewise, an antibody is a binding partner to its antigen, and vice versa.

"Colloids", as used herein, means nanoparticles, i.e. very small, self-suspendable or fluid-suspendable particles including those made of material that is, e.g., inorganic or organic, polymeric, ceramic, semiconductor, metallic (e.g. gold), non-metallic, crystalline, amorphous, or a combination. Typically, colloid particles used in accordance with the invention are of less than 250 nm cross section in any dimension, more typically less than 100 nm cross section in any dimension, and in most cases are of about 2-30 nm cross section. One class of colloids suitable for use in the invention is 10-30 nm in cross section, and another about 2-10 nm in cross section. Colloids may be associated with a binding partner, for example, an antibody. As used herein this term includes the definition commonly used in the field of biochemistry.

As used herein, a component that is "immobilized relative to" another component either is fastened to the other component or is indirectly fastened to the other component, e.g., by being fastened to a third component to which the other component also is fastened, or otherwise is transitionally associated with the other component. For example, a signaling entity is immobilized with respect to a binding species if the signaling entity is fastened to the binding species, is fastened to a colloid particle to which the binding species is fastened, is fastened to a dendrimer or polymer to which the binding species is fastened, etc.

"Signaling entity" means an entity that is capable of indicating its existence in a particular sample or at a particular location. Signaling entities of the invention can be those that are identifiable by the unaided human eye, those that may be invisible in isolation but may be detectable by the unaided human eye if in sufficient quantity (e.g., colloid particles), entities that absorb or emit electromagnetic radiation at a level or within a wavelength range such that they can be readily detected visibly (unaided or with a microscope including an electron microscope or the like), optically, or spectroscopically, entities that can be detected electronically or electrochemically, such as redox-active molecules exhibiting a characteristic oxidation/reduction pattern upon exposure to appropriate activation energy ("electronic signaling entities"), or the like. Examples include dyes, pigments, electroactive molecules such as redox-active molecules, fluorescent moieties (including, by definition, phosphorescent moieties), up-regulating phosphors, chemiluminescent entities, electrochemiluminescent entities, or enzyme-linked signaling moieties including horseradish peroxidase and alkaline phosphatase. "Precursors of signaling entities" are entities that by themselves may not have signaling capability but, upon chemical, electrochemical, electrical, magnetic, or physical interaction with another species, become signaling entities. An example includes a chromophore having the ability to emit radiation within a particular, detectable wavelength only upon chemical interaction with another molecule. Precursors of signaling entities are distinguishable from, but are included within the definition of, "signaling entities" as used herein.

In one aspect, the invention may be used to provide a series of fluids to a device such as a microfluidic device. The microfluidic device may be one of those described herein or may be any other microfluidic device. For example, fluids may be flowed in series to a reaction site in a microfluidic assay. The fluids may be gases, aqueous liquids, or non-aqueous liquids. Fluids and fluid components may include, for example, reagents, rinses, pre-rinses, fixatives and stains. The fluids may be flowed to one or more reaction sites with little or no mixing between different reagents. A series of rinse solutions may be separated by a separation plug, allowing a first rinse solution to pass completely over a reaction site before a second rinse solution is applied to the site.

Figure 12:
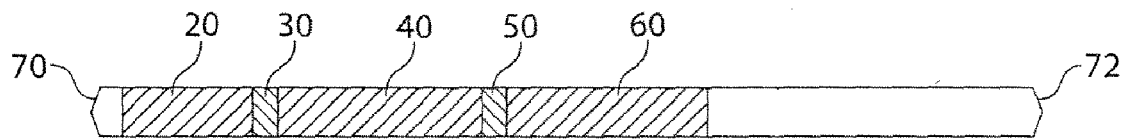
FIG. 12 is a schematic illustration of a vessel containing fluid plugs.

In one aspect, a vessel is provided to contain, store, protect and/or transport two or more fluids. As used herein, vessels include cartridges and tubes. A vessel may contain two or more distinct fluids separated by a third fluid that is immiscible with both. Any number of distinct fluids may be contained in a vessel. For example, FIG. 12 illustrates in longitudinal cross-section an embodiment where the vessel is a tube 10 that includes a reagent solution plug 20 followed by an air plug 30, followed by a rinse solution plug 40. An additional air plug 50 may separate the first rinse solution plug 40 from a second rinse solution plug 60. The ends of the tube 70 and 72 may be sealed, for example, to retain the plugs and to prevent contamination from external sources. The liquid plugs may retain their relative positions in the tube and may be prevented from contacting each other by the interspaced air plugs. The tube dimensions and materials of construction may be chosen to help fluid plugs retain their position and remain unmixed.

Reagents and other fluids may be stored for extended lengths of time in the vessel. For example, reagents may be stored for greater than 1 day, 1 week, 1 month or 1 year. By preventing contact between fluids, fluids containing components that would typically react or bind with each other are prevented from doing so, while being maintained in a continuous chamber.

Fluids may be transferred from the vessel to be used in a process, for example, to participate in a reaction or assay. Fluids may be transferred from the vessel by applying pressure or vacuum after removing or piercing the seal at ends 70 and 72. In other embodiments, the vessel need not be sealed and fluid flow can be started by applying an external force, such as a pressure differential. One end of the vessel, for example, end 70, can be in or can be placed in fluid communication with another device that will receive the fluids from the vessel. Such a device may include, for example, a reaction site of a reactor or an assay.

A vessel containing fluid plugs may be put in fluid communication with a reaction site and fluids may be flowed from the vessel to the reaction site. For instance, the fluids may be flowed to a microfluidic immunoassay, some embodiments of which are described herein. The vessel containing the fluid plugs may be separate from a device including the reaction site or may be part of the same platform. Fluid may be flowed to the reaction site by, for example pushing or pulling the fluid through the vessel. Fluids can be pushed to the reaction site using, for example, a pump, syringe, pressurized vessel, or any other source of pressure. Alternatively, fluids can be pulled to the reaction site by application of vacuum or reduced pressure on a downstream side of the reaction site. Vacuum may be provided by any source capable of providing a lower pressure condition than exists upstream of the reaction site. Such sources may include vacuum pumps, venturis, syringes and evacuated containers.

In one set of embodiments, a vessel may contain fluid plugs in linear order so that as fluids flow from the vessel to a reaction site they are delivered in a predetermined sequence. For example, an assay may receive, in series, an antibody fluid, a rinse fluid, a labeled-antibody fluid and a rinse fluid. By maintaining an immiscible fluid (a separation fluid) between each of these assay fluids, the assay fluids can be delivered in sequence from a single vessel while avoiding contact between any of the assay fluids. Any immiscible fluid that is separating assay fluids may be applied to the reaction site without altering the conditions of the reaction site. For instance, if antibody-antigen binding has occurred at a reaction site, air can be applied to the site with minimal or no effect on any binding that has occurred.

In one embodiment, at least two fluids may be flowed in series from a common vessel, and a component of each fluid may participate in a common reaction. As used herein, "common reaction" means that at least one component from each fluid reacts with the other after the fluids have been delivered from the vessel, or at least one component from each fluid reacts with a common component and/or at a common reaction site after being delivered from the vessel. For example, a component of the first fluid may react with a chemical or biological entity that is downstream of the vessel. A chemical or biological entity may form a reaction site and may be, for example, a sample, a biological or chemical compound, a cell, a portion of a cell, a surface or a substrate. The chemical or biological entity may be fixed in position or may be mobile. A component from the second fluid may then react and/or associate with the component from the first fluid that has reacted with the downstream chemical or biological entity, or it may react or associate with the chemical or biological entity itself. Additional fluids may then be applied, in series, to the biological or chemical entity to effect additional reactions or binding events or as indicators or signal enhancers.

Pre-filling of the vessel with reagents may allow the reagents to be dispensed in a predetermined order for a downstream process. In cases where a predetermined time of exposure to a reagent is desired, the amount of each fluid in the vessel may be proportional to the amount of time the reagent is exposed to a downstream reaction site. For example, if the desired exposure time for a first reagent is twice the desired exposure time for a second reagent, the volume of the first reagent in the vessel may be twice the volume of the second reagent in the vessel. If a constant pressure differential is applied in flowing the reagents from the vessel to the reaction site, and if the viscosity of the fluids is the same or similar, the exposure time of each fluid at a specific point, such as a reaction site, may be proportional to the relative volume of the fluid. Factors such as vessel geometry, pressure or viscosity can also be altered to change flow rates of specific fluids from the vessel.

Another aspect of the invention centers around filling a vessel with fluid plugs. In one embodiment, the vessel is a tube and the tube is filled sequentially with a series of fluid plugs separated by plugs of immiscible separating fluids. Fluids may be disposed in the tube in any manner that allows two or more fluid plugs to be separated by one or more separation fluid plugs. For example, fluids may be pumped into the tube under pressure or pulled into the tube by vacuum.

In one embodiment, a first end of the tube may be connected to a vacuum source. The tube may be pre-filled with a fluid, such as a buffer, that exhibits greater viscosity than air and may allow for more precise control of fill rates than if the tube were simply filled with air. Some, or all, of any fluid that is used to pre-fill the tube may be expelled from the tube during the filling process. Between the portion of the tube to be filled and the vacuum source may be placed a valve that can be opened or closed to provide vacuum to the tube. The opposing end of the tube may be placed in a reservoir that may be, for example, a vial or a well in a 96 well plate. The reservoir may contain a fluid such as a buffer, reagent fluid, rinse solution, precursor or separating fluid. The valve may be opened for a time period long enough to draw in the desired amount of fluid from the reservoir. The valve may be controlled manually or by a controller such as computer. After the valve has closed, the opposing end of the tube can be removed from the fluid reservoir and a second fluid plug may be drawn into the tube. If air is the second fluid, the valve may be actuated while the end of the tube is suspended in air, not in a reservoir. When an air plug of suitable length has been aspirated into the tube, the valve may be closed and the opposing end of the tube may be placed in a fluid reservoir that may be the same as, or different from, the first. The valve may then be opened again for a length of time appropriate for aspirating the desired plug size. This may be followed by another separating fluid plug that may be the same or different from the first. The procedure may be repeated until a predetermined sequence and quantity of fluids have been aspirated into the tube. In some cases, the tube can then be sealed, at one or both ends. Multiple tubes may be aspirated in parallel using a common controller, such as a computer. Fluids may be drawn from common or separate vessels when more than one tube is filled.

In another embodiment, vessels such as tubes may be filled without a vacuum pump or without a source of electric power. For example, a hand-operated syringe may provide a vacuum source for aspirating fluids. The syringe plunger may be withdrawn a specific distance to provide for aspiration of a specific amount of fluid into an opposing end of a tube. Valving may not be necessary. Multiple tubes may be filled in parallel.

In one aspect, a vessel may be used to retain two or more fluids that can be delivered in series from the vessel. The vessel may be any shape and size and may be made of any material appropriate for retaining the fluids which it is designed to hold. Depending on the fluids, this material may be, for example, glass, metal, or a polymer. Polymers may include, for example, thermoplastics such as polyethylene and polypropylene, polycarbonates, polystyrene, PTFE, PET, and others known to those skilled in the art.

In some embodiments, the vessel is a tube. Tubes may be preferred as they are readily available in different diameters, lengths and materials. Tubes may be flexible and may be translucent or transparent. Fluid plugs in a tube may be measured linearly as an indication of the volume of the plug. The tube may have a consistent or variable inner diameter and may have a length-to-internal diameter ratio greater than 10 to 1, greater than 50 to 1, or greater than 100 to 1. Depending upon the application, tubes of any diameter may be used, and in many applications the tube may have an inner diameter of less than 1 cm, less than 5 mm, less than 1 mm, less than 500 microns, less than 200 microns, less than 100 microns, or less than 50 microns. A tube with a greater length-to-internal diameter ratio may be useful in visually indicating the amount of each fluid contained in the tube. For instance, a linear measurement of a fluid plug in a tube of known inner diameter may give an accurate indication of the volume or the relative volume of the fluid.

The vessel, if a tube or another shape, may include two or more branches or sections that may be in fluid communication with each other and with the remaining interior of the vessel. In some embodiments, a tube may have two, three, four or more branches that may be interconnected. The branches and branch junctions may or may not include valves. Valves may be used to temporarily segregate one or more branches, and any liquid contained therein, from the remainder of the tube.

In one embodiment, a tube may include a "Y" shaped branch at one end, for instance, an upstream end. Each branch of the Y may contain a fluid that reacts with the fluid in the other branch to form a third fluid. Drawing each fluid from each branch into a common tube may provide an environment for allowing the two fluids to react. The two branches may join at a section, or lead to a section, that is of sufficient dimensions to promote turbulent flow and therefore mixing of the two fluids. For examples of different geometries, see U.S. patent application Ser. No. 09/954,710, which is incorporated by reference in its entirety herein.

In some embodiments, the material used for the vessel may be highly wetable. In other embodiments, however, the material used for the vessel, and in particular, the material used for the interior surface of the vessel, may exhibit low wetability. For example, when aqueous solutions are to be contained in the vessel, the interior surface of the vessel may exhibit low wetability for aqueous solutions. If the interior surface of the vessel is less wetable, it may be less likely that a fluid will flow along the surface. On a highly wetable surface, an aqueous solution may flow along the walls of the vessel and may be more likely to come into contact with other fluids contained in the vessel. A less wetable surface may allow for the use of higher inner diameter to length ratios for tubes, cartridges or other vessels while maintaining distinct fluid plugs during storage, shipment and/or use. Surface energy is indicative of the wetability of a surface and it may be preferred that the vessel, or the interior surface of the vessel, have a surface energy of less than 40 dynes/cm, less than 35 dynes/cm, less than 32 dynes/cm or less than 30 dynes/cm. Some polymers that may exhibit surface energies in these ranges include polypropylene, polyethylene and PTFE.

The vessel may also be made of a material having low adsorbance characteristics for fluid components that may be retained in the vessel. For example, if a vessel is to retain a fluid containing proteins, it may be preferred to use a vessel made of a material that does not adsorb proteins. If the interior surface of the vessel does exhibit a tendency to adsorb a component of a fluid, the surface may be pretreated to reduce that tendency. For example, a polymer surface may be treated with surfactants such as Tween 20 or blocking proteins such as albumin and/or casein to reduce its tendency to adsorb proteins. For other examples of treating surfaces, see U.S. patent application Ser. No. 09/907,551, filed Jul. 17, 2001, titled "Surfaces that Resist the Adsorption of Biological Species," which is incorporated by reference in its entirety herein.

The vessel may be disposable or reusable and when in the form of a tube, may be convoluted, for example in a serpentine pattern, to extend the length that can fit in a given space.

One or more ends of the vessel may be sealed in order to protect and retain any liquids that may be stored within. Some materials, in particular, thermoplastics and glass, may be sealed by melting the ends. Ends may also be sealed by crimping, capping, stoppering or fixing any material to the end to prevent flow or evaporation of fluid from the vessel. In one embodiment, a fluid having low volatility, such as an oil or glycol may be placed in the end of a tube to help prevent evaporation and/or movement of other fluids contained therein.

In various embodiments, any type of fluid or fluids may be used. Fluids include liquids such as solvents, solutions and suspensions. Fluids also include gases and mixtures of gases. When multiple fluids are contained in a vessel (such as a tube) the fluids may be separated by another fluid, that is preferably immiscible in each of the first two fluids. For example, if a tube contains two different aqueous solutions, a separation plug of a third fluid may be immiscible in both of the aqueous solutions. When aqueous solutions are to be kept separate, immiscible fluids that can be used as separators may include gases such as air or nitrogen, or hydrophobic fluids that are substantially immiscible with the aqueous fluids. Fluids may also be chosen based on the fluid's reactivity with adjacent fluids. For example, an inert gas such as nitrogen may be used in some embodiments and may help preserve and/or stabilize any adjacent fluids. An example of an immiscible liquid for separating aqueous solutions is perfluorodecalin. The choice of a separator fluid may be made based on other factors as well, including any effect that the separator fluid may have on the surface tension of the adjacent fluid plugs. It may be preferred to maximize the surface tension within any fluid plug to promote retention of the fluid plug as a single continuous unit under varying environmental conditions such as vibration, shock and temperature variations. Separator fluids may also be inert to any reactive site to which the fluids will be supplied. For example, if a reactive site includes a biological binding partner, a separator fluid such as air or nitrogen may have little or no effect on the binding partner. The use of a gas as a separator fluid may also provide room for expansion within the vessel should liquids contained in the vessel expand or contract due to changes such as temperature (including freezing) or pressure variations.

Fluids can be transferred from a vessel for use in a chemical or biochemical process. By applying an external force to the vessel such as pressure, suction, or g-forces, fluids may be flowed from a vessel at constant or varying flow rates. Fluids may also be drawn from a vessel by capillary action. Pressure may be applied upstream of the fluids to be flowed from the vessel and pressure sources may include pumps, such as electric or manual pumps, syringes, or pressurized containers. Suction may be applied to the downstream side of the vessel by using a vacuum or partial vacuum source such as a pump, syringe, evacuated container venturi or other source of reduced pressure.

In one embodiment, a vacuum source is used to flow liquids from the vessel. To control the flow of liquids from the vessel, for instance, when liquids are to be flowed over a reaction site at a specific rate, it may be preferred to apply a constant partial vacuum pressure to the downstream side of the vessel. Accurate vacuum pressures can be provided by vacuum pump, by a portable battery-powered pump or by a syringe. Vacuum pressure less than 1.0, 0.99, 0.95, 0.9, 0.8, 0.7, 0.6, 0.5, 0.3, 0.2, or 0.1 atmospheres may be used.

In some embodiments, a vacuum or partial vacuum may be applied to the vessel without the use of electrical power. For example, a syringe including a syringe barrel and plunger may be used to provide a source of vacuum. If the vessel is in communication with a reaction site, such as that in a microfluidic assay, the vacuum source, in this case, a syringe, may be attached downstream of the reaction site. Vacuum may be applied by placing the tip of the syringe barrel in fluid communication with the downstream side of the vessel retaining the fluids. If a total vacuum, or close to total vacuum, is desired, then all air may be expelled from the syringe by completely depressing the syringe plunger to the bottom of the barrel and subsequently attaching the barrel to the vessel. To provide less than a total vacuum, the syringe barrel may be partially filled with air prior to withdrawing the plunger to produce vacuum. For example, if a 10 cc syringe is used, a syringe barrel may be filled to 5 ccs with air and the plunger withdrawn to a total volume of 10 ccs to provide a vacuum equal to one-half atmosphere. Likewise, 0.75 atmosphere may be applied by filling a 10 cc syringe with 7.5 ccs of air and then withdrawing the plunger to the full 10 cc mark. A holding device such as a clip or a notch in the syringe barrel may be used to hold the plunger in the constant position after it is withdrawn. If the internal volume of the syringe used is significantly greater than the volume of fluids to be drawn from the vessel, the vacuum pressure applied to the vessel may be substantially constant from the beginning to the end of the drawing process. In some embodiments, the volume of the syringe used may be greater than 10×, 100× or 1,000× the volume of the fluid or fluids to be drawn.

When the syringe is filled with air to a specific volume, the air in the syringe barrel may be at atmospheric pressure, regardless of where the process is performed. Compared to providing a partial vacuum at a fixed absolute pressure, such as with an evacuated container, this manual syringe technique may be useful under conditions of varying ambient pressure, such as at different altitudes, as the method may produce a more consistent pressure differential across the vessel and/or the reaction site, regardless of the ambient air pressure. This may aide in drawing fluids at a predetermined rate and thus subject a reaction site to a more precise predetermined residence time for each fluid.

In another aspect, the vessel may be used to store fluids. In various embodiments, fluids may be stored in the vessel for greater than 10 seconds, one minute, one hour, one day, one week, one month, or one year. While they are stored, fluids may be kept separated by immiscible separation fluids so that fluids that would react with each other when in contact may be stored for extended periods of time in a common vessel. The fluids may be stored so that they are statically maintained and do not move in relation to their position in the vessel. Fluids may shift slightly or vibrate and expand and contract while being statically maintained. The common vessel may have an absence of inner walls or other dividers to keep the fluids apart and fluids may be separated by nothing more than a separation fluid. When stored in a static state, the fluids may be stored at reduced temperatures, such as less than 4° C., less than 0° C., or less than −10° C. Fluids may also be exposed to elevated temperatures such as greater than 25° C., greater than 35° C. or greater than 50° C. Fluids may be shipped from one location to the other by surface or air without allowing for mixing of reagent fluids contained in the vessel. The amount of immiscible separation fluid may be chosen based on the end process with which the fluids are to be used as well as on the conditions to which it is expected that the vessel will be exposed. For example, if the vessel is expected to receive physical shock or vibration, larger plugs of immiscible separation fluid may be used. In this manner, distinct fluids within a vessel may avoid mixing.

In another embodiment, the vessel containing the fluids may be stored along with a device including a reaction site such as an assay device or a chemical or biochemical reactor. The vessel and device may be integrally connected or constructed and arranged to be integrally connected. Thus, a full reagent set may be serially lined up in the vessel and ready for application to the reaction site upon applying, for example, pressure or vacuum to an appropriate end of the vessel or device.

A vessel containing a series of fluid plugs may be connected to a downstream device for participation in a chemical or biochemical reaction. An end of the vessel, for example an end of a tube or cartridge, may be connected to a device so that the two are in fluid communication. This may be done directly, by inserting a tube end into an inlet on the device or may be done indirectly by attaching via an intermediate connector, such as a length of tubing. In some cases, dead space at the connection point may be minimized to decrease, for example, delay, mixing, or the formation of turbulent flow. The connection may be vacuum-tight. In some embodiments, the inner diameter of the connector may be less than 1×, 3× or 5× the inner diameter of either the vessel or the device. Some softer polymers may provide for a better connection than harder polymers. For example, a device made of PDMS may provide for a secure connection with minimal dead volume.

In another embodiment, a vessel including fluid plugs may be integrally connected to a device that includes a reaction site. For example, the vessel and device may be formed on a common platform such as a microfluidic chip. The device and vessel may be in fluid communication so that when a vacuum or partial vacuum is applied downstream of a reaction site, fluid plugs are drawn from the vessel. Likewise, pressure applied upstream of the fluid plugs may push the fluids into the device and apply them to the reaction site.

More than one vessel may be integrally connected or non-integrally connectable to a device including a reaction site. For example, if two vessels are connected to the upstream side of a device, the fluids in one of the vessels may be passed over the reaction site by unsealing an upstream end of the first device while maintaining a seal on the upstream side of the second device. Vacuum applied to the downstream side of the device will draw reagents from the first vessel but not the second. In a similar manner, two or more devices including reaction sites may be connected to a single vessel containing fluids, and the fluids may be drawn through a chosen device by, for example, applying vacuum to that device while leaving the other device or devices sealed.

Samples of all types may be used in conjunction with different embodiments. Samples may include chemical samples such as water, solvents, extracts, and environmental samples. Samples may also include biological samples such as whole blood, serum, plasma, tears, urine and saliva. A sample being examined with an assay or reacted in a reactor may be transferred either to a reaction device or to a vessel containing reagent fluids. For example, a sample of whole blood may be placed in the inlet of an assay device and may be flowed over the reaction site by using vacuum or pressure. This may occur prior to connecting the vessel or prior to flowing reagents from the vessel to the reaction site. Alternatively, the sample may be placed in a vessel containing reagent fluids. For instance, a whole blood sample of measured volume may be injected into the downstream end of a tube containing fluid reagents. The tube may then be connected to the assay device and, upon application of vacuum or pressure, the sample may be applied to the reaction site in advance of the reagents that are flowed serially from the tube. In another embodiment, some reagents may be flowed to the reaction site, followed by a sample, which is in turn followed additional reagents. In yet other embodiments, the sample may be flowed last.

In one embodiment, a device including a reactive site may be integrally or non-integrally connected to a sampling device, such as a sampling tube. The sampling tube may have one end associated with a channel or chamber housing the reaction site. An opposing end of the tube may be dipped into a sample source (that may be a container or may be a subject)

to be analyzed or reacted. By applying vacuum downstream of the reaction site, sample may be drawn into the sample tube and may either be maintained in the sample tube or drawn to the reaction site. When a predetermined amount of sample is obtained, the end of the sample tube may be removed from the sample source or the vacuum may be stopped. In some embodiments, the same sample tube may then serve as a connector between the device and a vessel holding reagent fluids. By placing the end of the sampling tube in fluid communication with the downstream side of the vessel containing fluids, the fluids may be drawn through the channel of the device in a method similar to how the sample was drawn through. In some cases, a first reagent fluid in the vessel may be chosen to help carry the sample, treat the sample, dilute the sample, or rinse the sample from the tube.

The invention provides a method and apparatus for determining a presence, qualitatively or quantitatively, of a component in a sample. The component may be a binding partner, such as an antibody or antigen, that may be indicative of a disease condition.

In one aspect, a sample from a subject can be analyzed with little or no sample preparation. The sample may also be obtained non-invasively, thus providing for a safer and more patient-friendly analytical procedure.

In another aspect, an assay providing high sensitivity and a low limit of detection, comparable to that of the most sensitive ELISA test, is provided. The assay can be run quickly and results may be permanent, allowing for reading the assay at any time after performing the test.

In another aspect, a sample is flowed over a surface associated with a prospective binding partner of a sample component. The assay can be performed in a channel of a microfluidic device allowing the sample to be flowed over a binding partner, for example, an antigen. Any antigen-antibody complex that forms may be associated with a metal colloid that provides a catalytic surface for the deposition of an opaque material, such as a layer of metal. Therefore, if antibody-antigen binding occurs in the microfluidic channel, the flowing of a metal precursor through the channel can result in the formation of an opaque layer, such as a silver layer, due to the presence of the catalytic metal colloid associated with the antibody-antigen complex. Any opaque layer that is formed in the microfluidic channel can be detected optically, for example, by measuring a reduction in light transmittance through the microfluidic channel compared to a portion of the channel that does not include the antibody or antigen. The opaque layer may provide an increase in assay sensitivity when compared to techniques that do not form an opaque layer.

As used herein, "fastened to or adapted to be fastened", in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "fastened" in this context includes multiple chemical linkages, multiple chemical/biological linkages, etc., including, but not limited to, a binding species such as a peptide synthesized on a polystyrene bead, a binding species specifically biologically coupled to an antibody which is bound to a protein such as protein A, which is attached to a bead, a binding species that forms a part (via genetic engineering) of a molecule such as GST or Phage, which in turn is specifically biologically bound to a binding partner covalently fastened to a surface (e.g., glutathione in the case of GST), etc. As another example, a moiety covalently linked to a thiol is adapted to be fastened to a gold surface since thiols bind gold covalently. Similarly, a species carrying a metal binding tag is adapted to be fastened to a surface that carries a molecule covalently attached to the surface (such as thiol/gold binding) which molecule also presents a chelate coordinating a metal. A species also is adapted to be fastened to a surface if a surface carries a particular nucleotide sequence, and the species includes a complementary nucleotide sequence.

A microfluidic device of the invention can be fabricated of a polymer, for example an elastomeric material such as poly (dimethylsiloxane) (PDMS) using rapid prototyping and soft lithography. For example, a high resolution laser printer may be used to generate a mask from a CAD file that represents the channels that make up the fluidic network. The mask may be a transparency that may be contacted with a photoresist, for example, SU-8 photoresist (MicroChem), to produce a negative master of the photoresist on a silicon wafer. A positive replica of PDMS may be made by molding the PDMS against the master, a technique known to those skilled in the art. To complete the fluidic network, a flat substrate, for example, a glass slide. silicon wafer, or polystyrene surface may be placed against the PDMS surface and may be held in place by van der Waals forces, or may be fixed to the PDMS using an adhesive. To allow for the introduction and receiving of fluids to and from the network, holes (for example 1 millimeter in diameter) may be formed in the PDMS by using an appropriately sized needle. To allow the fluidic network to communicate with a fluid source, tubing, for example of polyethylene, may be sealed in communication with the holes to form a fluidic connection. To prevent leakage, the connection may be sealed with a sealant or adhesive such as epoxy glue.

In one embodiment, as shown in FIG. 1, a microfluidic device 110 can be used to provide a substrate on which to perform the assay. Methods of manufacturing such a microfluidic device are provided in U.S. Pat. No. 6,645,432, incorporated by reference in its entirety herein.

A series of microfluidic channels, 120, 122, and 124, can be used to flow sample and metal precursor across the surface 130 of the microfluidic device. A binding partner, for example, an antigen or antibody, may be disposed on surface 130 at portion 140. Portion 140 may include a stripe of binding partner, as shown, transversing two or more channels. Alternatively, a binding partner may be disposed on a portion limited to a single channel. Multiple binding partners may be disposed in a single channel and may overlap or be segregated from each other.

Binding partners immobilized at a region or portion of a region can be immobilized in essentially any manner, and many immobilization techniques suitable for use with the invention are known in the art. See U.S. patent application Ser. Nos. 10/654,587 and 09/578,562, which are incorporated by reference in their entirety herein. Immobilization can be done in a way such that the species are randomly oriented relative to the surface (i.e., each immobilized species can be oriented, relative to the surface, randomly), or greater control of the orientation of species relative to the surface can be provided. For example, where proteins are immobilized at the surface, they can be oriented such that their binding sites for the assay are oriented generally away from the surface, maximizing their binding capacity or availability. One technique for doing so, described in U.S. Pat. No. 5,620,850, incorporated herein by reference, involves synthesizing the protein with a polyamino acid tag such as, for example, a sequence of 6 histidines, at a location generally opposite the protein's relevant binding site, providing a metal chelate, such as nitrilotriacetic acid, chelating a metal ion such as nickel in such a way that at least two coordination sites on nickel are free for binding to the polyamino acid tag, and allowing the tag to coordinate to the metal ions, thus immobilizing the protein at the region or portion of a region in an advantageous orientation. A metal chelate such as this can be immobilized at the region in any of a number of ways. One way involves forming a self-assembled monolayer (SAM) at the region, terminating in the metal chelate, as described in the above-referenced U.S. Pat. No. 5,620,850. For example, a thin, essentially transparent thin gold layer can be deposited at the region, and SAM-forming alkyl thiols, terminating in a metal chelate, can be deposited on the gold layer as a SAM. Other chemistry, described in U.S. Pat. No. 5,620,850 and other references, and known to those of ordinary skill in the art, can be used to form such a SAM on a region defined by a variety of base materials.

To run the assay, a sample, such as a biological sample taken from a subject, is flowed through one or more microchannels 120, 122, or 124, in the direction shown by the arrows. The sample may be a liquid sample, but in some embodiments need not be diluted, purified or treated prior to analysis. The sample may be flowed through the microchannel at a rate sufficient to allow a component of the sample to bind with a binding partner immobilized at portion 140. By actively flowing the sample through the channel, the reactive portion 140 is repeatedly exposed to components of the sample, improving reaction kinetics and resulting in an increased formation of any binding pairs. After an adequate amount of flow of sample through microchannel 120, e.g., when detectable binding pairs have formed, a fluid containing a metal colloid associated with a second binding partner of the sample component is flowed to the microchannel, allowing the metal colloid to bind with any sample component that has been associated with portion 140 of the microchannel.

After the metal colloid has been given the opportunity to bind with any binding partner at portion 140, a metal precursor can be flowed through channel 120 in a similar manner as was the metal colloid. The metal precursor is flowed through the microchannel at a concentration and a rate that allows an opaque layer to be formed wherever a threshold number of metal colloids have been associated with the surface. Thus, if a gold conjugated antibody is used as a metal colloid, a silver nitrate solution may be used to electrolessly deposit a silver layer on the portion of the channel associated with the gold conjugated antibody. At the completion of this portion of the assay, surface 130 of the microfluidic network may include, in successive layers, an antigen such as HIV antigen, a sample component of an HIV antibody obtained from a subject, a metal colloid such as gold-labeled anti-human IgG, and an opaque layer of metal, such as silver, that has been electrolessly deposited on the metal colloid. Rinsing solutions may be flowed through the channel before or after each of the steps.

In addition to depositing metal on any metal colloids that may be associated with portion 140 of microchannel 120, the metal precursor may also be deposited on metal that has previously been electrolessly deposited on the gold-conjugated antibody. In this manner, an opaque material may be formed over some or all of portion 140 allowing for detection by, for example, the unaided eye or an optical detection device. The opaque material may be a continuous material rather than, for example, independent particles, and may include a horizontal dimension that, in a dimension measured in substantially the same plane as surface 130, measures greater than 1 micron, greater than 10 microns, or greater than 100 microns.

In some cases, an opaque layer may form a web or honeycomb of material that includes passages allowing light to be transmitted therethrough. As additional material is deposited, these passages may become smaller, allowing less and less light to be transmitted through the material. As the passages disappear, the amount of light transmittance may be reduced to zero, providing for a completely opaque material.

Figure 2:
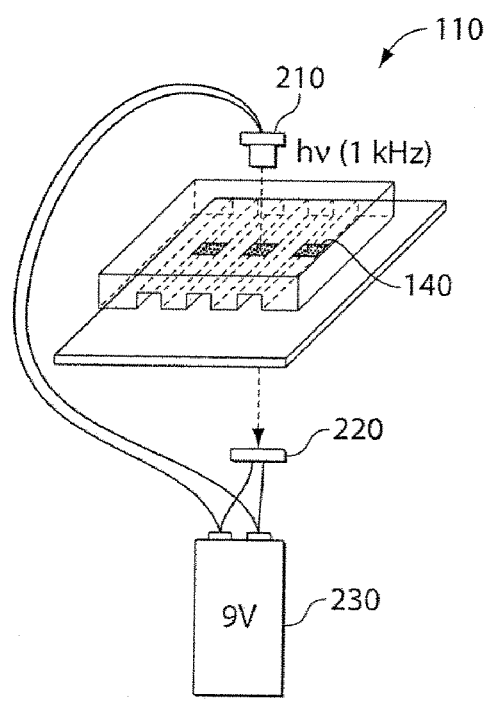
FIG. 2 is an illustration of an assay including a detector.
Figure 3:
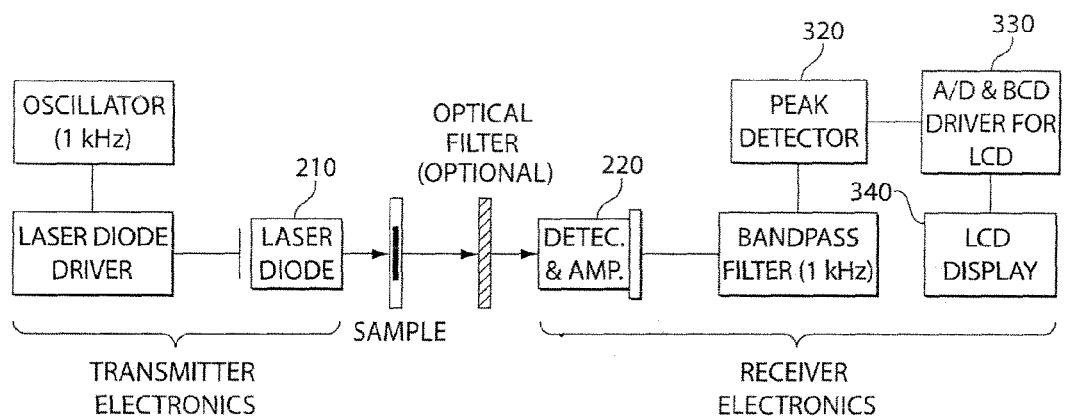
FIG. 3 is a schematic illustration of an optical detector.
Figure 9:
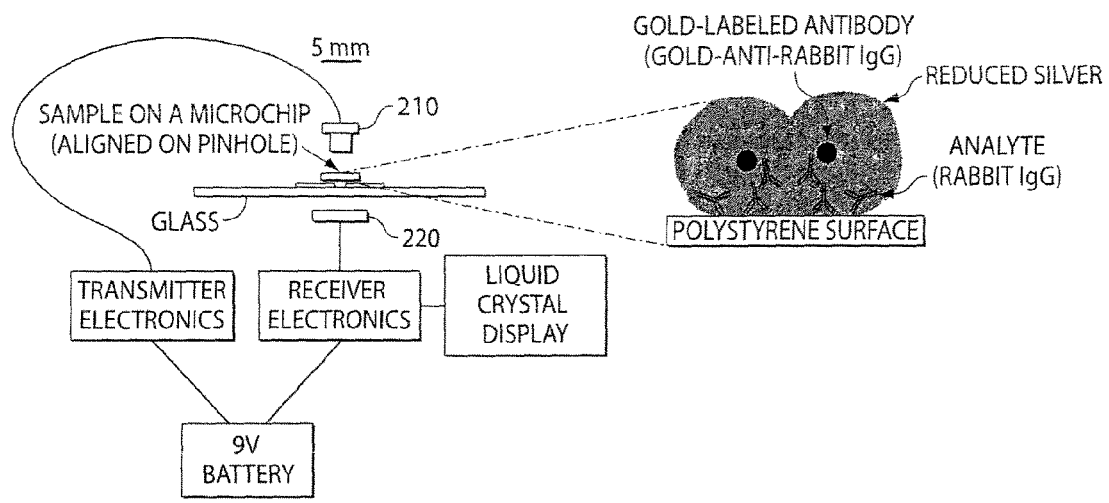
FIG. 9 provides a side view of an assay detection system.

After an opaque layer has been formed, detection of the opaque layer, and therefore determination of the presence of a binding partner, may be determined by visually examining the microfluidic device or by using a detector such as an optical detector. One embodiment of an optical detector is depicted in FIGS. 2, 3 and 9. FIG. 2 illustrates microfluidic device 110, as shown in FIG. 1. Also included is light source 210, here an oscillator-modulated laser diode, and a detector 220, such as an optical IC. As illustrated in the schematic diagram of FIG. 3, the detector signal may be amplified and passed through a bandpass filter centered at the same frequency as the oscillator controlling the light source. The output may then be passed to an A/D converter which can then provide an output on a readout, such as an LCD display. Both the light source and the detector may be powered by a 9 volt battery.

In one aspect, the invention provides an apparatus and method for analyzing a sample using continuous flow. Typically, existing methods such as ELISA and other sandwich assays use a 96 well plate, or similar, for containing a sample for the immunoassay. These methods can expose an antibody or an antigen to a sample component in a fluid, but the fluid is not flowed past the antibody or antigen and diffusion is relied on for bringing binding partners into proximity with each other. The present invention may allow for increased opportunities for binding of a sample component to a potential binding partner at similar or lower concentrations of sample component than previous methods. By flowing a sample containing one binding partner past a surface presenting the other binding partner, a greater number of potential binding partners are placed in proximity to each other than would occur via simple diffusion. In one embodiment, the sample is flowed through a micro-channel providing the benefits of flowing one binding partner past a second binding partner while requiring a small sample, for example, less than 10 micro liters, less than 1 micro liter, or less than 100 nanoliters of sample. The microchannel may be of a material transparent to light that is used to detect the formation of an opaque material in the channel so that any absorbance or transmittance of light through a portion of the channel can be attributed to the formation of an opaque layer.

Because immunoassays detect signaling entities, such as enzyme-conjugated secondary antibodies that are dissolved or suspended in a fluid, a relatively long path length is required in order to obtain optimal sensitivity. Thus, one reason why immunoassays have not been applied in microfluidics is the short path length typically presented by microfluidic devices. For example, a microfluidic device may have a channel having a thickness of less than 250 microns, less than 100 microns, or less than 40 microns. Therefore, any fluid filling a channel in this microfluidic device would present a perpendicular light pathway of less than 250, 100 or 40 microns. The present method may not be subject to these restrictions because it can use an opaque layer in the solid state, rather than a chromophore in a fluid. The opaque layer may have a thickness of less than 1 micron, of less than 100 nanometers or less than 10 nanometers. Even at these small thicknesses, a detectable change in transmittance can be obtained.

The geometry of the microfluidic channel may provide for the laminar flow of fluids through the channel, even at relatively high flow rates. Alternatively, turbulent flow may be employed by using even faster flow rates or devices such as microfluidic mixers. Such mixing may provide for a greater amount of contact between potential binding partners.

The presence, absence, or amount of an analyte in a sample may be indicated by the formation of an opaque material. Although the opaque material may be used to refract light or may be excited to emit light at a similar or different wavelength than the light to which the layer is exposed, the measurement of light transmission may be preferred due to, for example, lower equipment and operating costs, and ease of use. In some microchannels, an opaque layer may be visible to the naked eye and, in particular if reflective, may be detected without the use of instrumentation.

Any opaque material that forms can be a series of discontinuous independent particles, but in one embodiment is a continuous material that takes on a generally planar shape. The opaque material may have a dimension greater than 1 micron or greater than 10 microns. The opaque material may be a metal and is preferably a metal that can be electrolessly deposited. These metals include, for example, copper, nickel, cobalt, palladium, and platinum. A metal precursor is a material that can provide the source of the elemental metal for depositing on, for example, a metal colloid. For example a metal precursor may be a metallic salt solution such as silver nitrate. In one embodiment, a metal precursor may include 0.1% silver nitrate, 1.7% hydroquinone and 0.1 M citrate buffer at a pH of 3.5. Some other examples of electrolessly deposited materials can be found in Modern Electroplating, $4^{th}$ Edition, Schlesinger and Paunovic, Wiley, 2000. Metal precursors can be stored for long periods of time and may be stable for several years whereas optically active compounds may have much shorter shelf lives.

Any metal colloid associated with a surface may be widely scattered over a portion of the surface. For example, gold conjugated antibodies may be bound to sample components that are associated with the portion of the surface but spaces may exist between the gold conjugated antibodies, making them discontinuous. When a metal precursor is first exposed to these gold conjugated antibodies, the precursor may form particulates centered around individual metal colloids. As metal, e.g., silver, is deposited on these metal colloids, the particles become larger and soon the metal precursor may deposit metal not only on gold colloids but on metal that has been previously electrolessly deposited. For example, a silver nitrate solution may deposit silver metal on to silver metal particles that have previously been deposited on gold conjugated antibodies. Thus, as the silver layer continues to grow on silver, as well as on gold, areas that previously were independent particles or islands of metal can join to form a larger, continuous opaque material that can be easily detected. It has been found that a microfluidic system can provide for a relatively smooth, continuous layer of metal. The opaque material may have a thickness greater than 1, 10, 100 or 1000 nanometers. For some opaque materials, the material may become completely opaque at thicknesses greater than about 100 nm. However, in some embodiments, such as when a honeycomb or similar structure is formed, thickness in some portions may be much greater while still allowing some light to be transmitted.

A variety of chemical and biological materials may be analyzed by the methods and apparatuses described herein. Analytes may include chemicals such as organic compounds and biological materials such as proteins, peptides, nucleic acids and antibodies.

Analytes include any analyte for which a binding partner can be found. Analytes that may be determined include specific proteins, viruses, hormones, drugs, nucleic acids and polysaccharides; specifically antibodies, e.g.: IgD, IgG, IgM or IgA immunoglobulins to HTLV-I, HIV, Hepatitis A, B and non A/non B, Rubella, Measles, Human Parvovirus B19, Mumps, Malaria, Chicken Pox or Leukemia; human and animal hormones, e.g.: human growth hormone (hGM, human chorionic gonadotropin WM; drugs, e.g.: paracetamol or theophylline; marker nucleic acids, e.g.; as for genetic finger printing analysis markers; polysaccharides such as cell surface antigens for HLA tissue typing and bacterial cell wall material. Chemicals that may be detected include explosives such as TNT, nerve agents, and environmentally hazardous compounds such as polychlorinated biphenyls (PCBs), dioxins, hydrocarbons and MTBE. Typical sample fluids include physiological fluids such as human or animal whole blood, blood serum, blood plasma, semen, tears, urine, sweat, saliva, cerebro-spinal fluid, vaginal secretions; in-vitro fluids used in research or environmental fluids such as aqueous liquids suspected of being contaminated by the analyte.

In cases where an antigen is being analyzed, a corresponding antibody can be the binding partner associated with a surface of a microfluidic channel. If an antibody is the analyte, then an appropriate antigen may be the binding partner associated with the surface. When a disease condition is being determined, it may be preferred to put the antigen on the surface and to test for an antibody that has been produced in the subject. Such antibodies may include, for example, antibodies to HIV.

A biological sample may be obtained noninvasively. The low level of detection capable with the invention allows for the use of samples that typically contain lower concentrations of antigens or antibodies than does blood. For example, useful samples may be obtained from saliva, urine, sweat, or mucus. By allowing samples to be obtained noninvasively, the methods of the invention can provide for increased throughput, safer sampling, and less subject apprehension.

Figure 4:
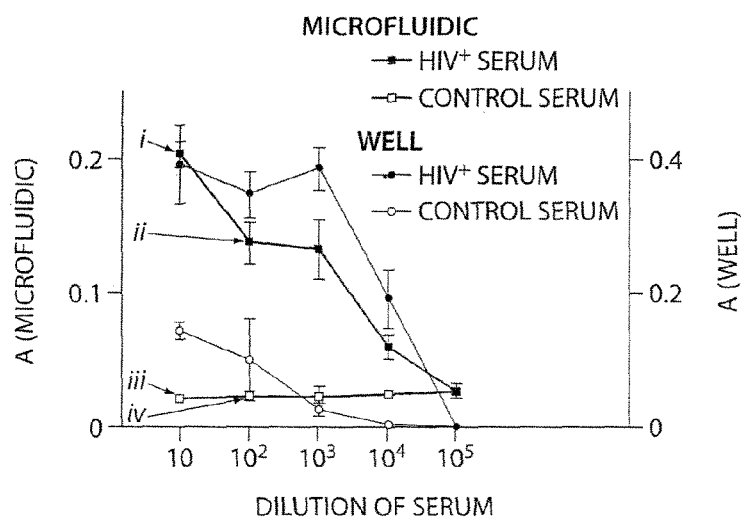
FIG. 4 is a graph illustrating absorbance versus analyte concentration.
Figure 5:
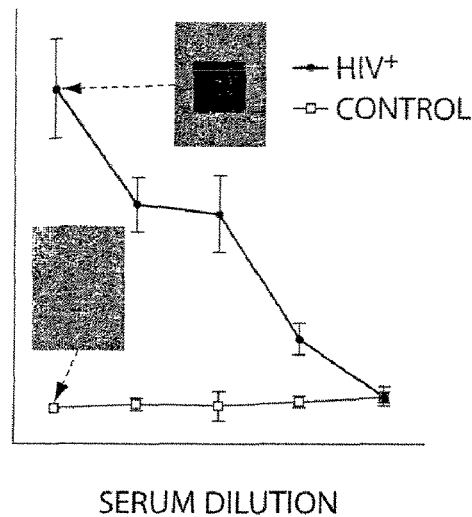
FIG. 5 illustrates graphically and in a photocopy of a micrograph the amount of opaque material present at high and low analyte concentrations.
Figure 6:
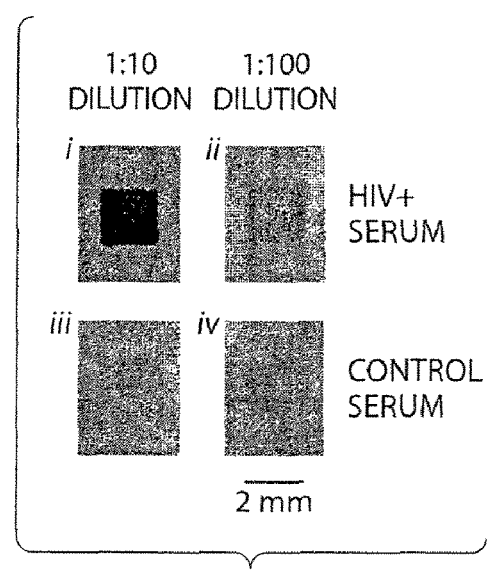
FIG. 6 provides photocopies of micrographs showing the formation of opaque material at various analyte concentrations.

The methods and apparatus of the present invention may be capable of obtaining limits of detection (LOD) comparable to those achievable by immunochromatographic assays as well as ELISA. For example, concentrations below 1 nM and even in the 100 pM range can be detected. The assay can be qualitative, quantitative, or both. As illustrated in FIG. 4, as the concentration of analyte increases, the apparent absorbance of the opaque material increases accordingly. In FIG. 4, the sample component (analyte) is HIV antigen and the sample is human serum. Different dilutions of these sera are shown and in FIG. 6 the formation of an opaque layer indicates a positive result when compared to control at dilutions of 1 to 10 and 1 to 100. Therefore, in addition to presence/absence type tests, a quantitative test may be provided. Such a quantitative test may be of interest, for example, to those monitoring antibody levels in a patient during treatment.

Sensitivity and Limits of Detection (LOD) of the method compare favorably to that obtainable with various state-of-art ELISA techniques. When compared to ELISA techniques using chemiluminescence, fluorescence and absorbance in assaying rabbit IgG, an embodiment of the invention using silver deposition provided comparable sensitivity and LOD numbers. Sensitivity and LOD were calculated using IUPAC definitions and are provided in Table 1 below. Higher sensitivity numbers indicate greater sensitivity and lower LOD numbers indicate a lower LOD.

TABLE 1

| Method | Sensitivity (normalized) | LOD (pM) |
| --- | --- | --- |
| Silver deposition | .08 | 89 |
| Chemiluminescence | .19 | 22 |
| Fluorescence | .12 | 163 |
| Absorbance | .04 | 55 |

In another embodiment, an assay is provided that requires less time to run than typical immuno-based assays such as ELISA. For example, using a microfluidic device of the present invention, incubation times for each reagent can be less than 10 minutes. For ELISA techniques using microwells, 1 to 3 hours incubation time is typically required for each reagent. Thus, the present method can provide a 6 to 18 fold decrease in incubation time. A portion of this time savings can be attributed to analyzing a sample directly without needing to purify, dilute or otherwise prepare a sample. For example, a saliva sample may be flowed across a channel without having been diluted, filtered, separated, or otherwise prepared. From the time a sample is obtained to when results are realized, a total time of less than one hour, less than 30 minutes, less than 20 minutes or less than 10 minutes may be realized. One reason for this increase in speed is an improved rate of binding between binding partners. This can be attributed, at least in part, to the flow system of the invention. Systems relying on diffusion, or capillary action are limited in the number of binding partners that can be exposed to each other over a given time period. Furthermore, as diffusion may be temperature dependent, the present invention, utilizing sample flow, may be more temperature independent than other methods, providing for a more robust assay in the field where temperatures may vary from above 40° C. to below 0° C.

In another embodiment, two or more parallel assays may be run. A single sample may be physically split into two or more samples using a microfluidic device. A microfluidic device may have a single input channel that branches into two, three, or more parallel channels. Parallel analysis may be performed at different threshold levels of a similar or identical analyte, or for different analytes at the same or different thresholds. A control may also be performed in parallel. Thus, with a single sample run, a sample can be analyzed for two or more analytes at any number of threshold concentrations. A control may also be run concurrently and may be useful in calibrating and/or verifying the detection method that is used. Once an opaque layer is formed, the assay may be stable for an extended period of time, for example, greater than one month or one year, so that assays may be collected and analyzed or re-analyzed at a later date.

Reagents and samples may be supplied to the assay using methods known to those skilled in the art, using methods described herein, or using methods described in United States Provisional Patent Application titled "Fluid Delivery System and Method," filed on even date, which is hereby incorporated by reference in its entirety herein.

A variety of determination techniques may be used. Determination techniques may include optically-based techniques such as light transmission, light absorbance, light scattering, light reflection and visual techniques. Determination techniques may also measure conductivity. For example, microelectrodes placed at opposite ends of a portion of a microfluidic channel may be used to measure the deposition of a conductive material, for example an electrolessly deposited metal. As a greater number of individual particles of metal grow and contact each other, conductivity may increase and provide an indication of the amount of conductor material, e.g., metal, that has been deposited on the portion. Therefore, conductivity or resistance may be used as a quantitative measure of analyte concentration.

Another analytical technique may include measuring a changing concentration of a precursor from the time the precursor enters the microfluidic channel until the time the precursor exits the channel. For example, if a silver nitrate solution is used, a silver sensitive electrode may be capable of measuring a loss in silver concentration due to the deposition of silver in a channel as the precursor passes through the channel.

Different optical detection techniques provide a number of options for determining assay results. In some embodiments, the measurement of transmission or absorbance means that light can be detected at the same wavelength at which it is emitted from a light source. Although the light source can be a narrow band source emitting at a single wavelength it may also may be a broad spectrum source, emitting over a range of wavelengths, as many opaque materials can effectively block a wide range of wavelengths. The system may be operated with a minimum of optical devices. For instance, the determining device may be free of a photo multiplier, may be free of a wavelength selector such as a grating, prism or filter, or may be free of a device to direct or columnate light such as a columnator. Elimination or reduction of these features can result in a less expensive, more robust device.

In one embodiment, the light source can be pulse modulated, for example, at a frequency of 1,000 Hz. To match the pulse modulated light source, a detector may include a filter operating at the same frequency. By using a pulse modulated light source it has been found that the system can be less sensitive to extrinsic sources of light. Therefore, the assay may run under various light conditions, including broad daylight, that might make it impractical to use existing techniques. Experimental results indicate that by using a pulse modulated light source and filter, results are consistent regardless of the light conditions under which the test is run.

The light source may be a laser diode. For example, an InGaAlP red semiconductor laser diode emitting at 654 nm may be used. The photodetector may be any device capable of detecting the transmission of light that is emitted by the light source. One type of photodetector is an optical integrated circuit (IC) including a photodiode having a peak sensitivity at 700 nm, an amplifier and a voltage regulator. If the light source is pulse modulated, the photodetector may include a filter to remove the effect of light that is not at the selected frequency.

EXAMPLES

An experiment was designed and run to evaluate the use of a heterogeneous immunoassay in combination with a cartridge containing a series of fluid plugs. All required reagents, except for the sample, were contained in the cartridge.

Photomasks for photolithography were obtained from PageWorks (Cambridge, Mass.). Negative photoresist SU8 was obtained from Microchem (Newton, Mass.). Poly(dimethylsiloxane) Sylgard184 (PDMS) was obtained from Dow Corning (Midland, Mich.). Polystyrene substrates were purchased from NUNC (Rochester, N.Y.). Rabbit, anti-rabbit and mouse immunoglobulin G (IgG) were purchased from Sigma (St-Louis, Mo.), and Alexa-488 donkey anti-sheep IgG was obtained from Molecular Probes (Eugene, Oreg.). A hand-operated vacuum pump and polyethylene tubing (Intramedic PE-60, 0.76 mm internal diameter and 1.22 mm external diameter) were purchased from VWR Scientific Products (Pittsburgh, Pa.). All other chemicals were of analytical grade and are available from chemical supply houses.

Preparation of a microfluidic platform. A PDMS replica with microchannels was prepared by rapid prototyping as described in U.S. Pat. No. 6,645,432 and in U.S. Patent Application titled "Assay Device and Method,", filed on even date herewith, both of which are incorporated by reference in their entireties herein. A microfluidic design was used to pattern stripes of antigen (two parallel channels, 30-mm long, 200-μm wide and 60-μm deep), and a second design was used to carry out the immunoassay (six parallel channels 50-mm long, 63-μm deep) These channels were composed of 5 sections of 10 mm each, with a width of 500 μm next to the inlet and outlet, 50 μm in the center (where the heterogeneous immunoassay takes place) and 250 μm in the intermediary segments. This geometry results in long channels (i.e. where the six inlets and six outlets can be geometrically separated from each other) with a limited resistance to flow (i.e. where fluids can be pumped in a hydrodynamic flow with a minimal pressure drop). The PDMS replica for patterning was sealed non-permanently (i.e. without plasma oxidation) to the polystyrene substrate and the two parallel channels were filled with a solution of 50 μg rabbit IgG and a solution of 50 μg mouse IgG solution in PBS. After a 90-minute incubation time at room temperature, the channels were emptied and rinsed twice with a fresh solution of 0.05% Tween in PBS. The PDMS slab was pealed off and the polystyrene substrate was rinsed with deionized water (conductivity larger than 18 MΩ) and dried with a nitrogen gun. Inlets and outlets were punched out in the second PDMS slab (for the immunoassay) using a sharpened medical needle with an outside diameter of 1.6 mm (gauge 16G1½). The holes left in the PDMS by this modified needle were large enough to insert PE-60 tubing and allowed a thigh seal between the cartridge and the microchannel. The second PDMS slab was non-permanently sealed onto the polystyrene substrate, with its microchannels oriented orthogonally to the stripes of antigen. The six microchannels were filled with a fresh solution of 0.05% Tween in PBS to block the exposed surface for at least two hours.

Heterogeneous Immunoassay—The cartridges were inserted into the inlets of the microfluidic channels and the outlets were connected to a source of vacuum. To ensure a steady source of vacuum throughout the assay, the hand-operated pump was connected to a 1 L round bottom flask, acting as ballast. Six PE-60 tubes in turn connected between the ballast and the outlets of the microfluidic chips. The assay was initiated by operating the pump until a −15 kPa pressure difference was achieved inside the ballast, resulting in the dispensing of the contents of the cartridges into the microfluidic channels. Fluorescence intensity on the stripe of antigen (i.e. where the immunocomplex is built) and outside the stripe (i.e. where non-specific binding and noise level are measured) were quantified and subtracted to obtain the signal intensity.

Figure 22:
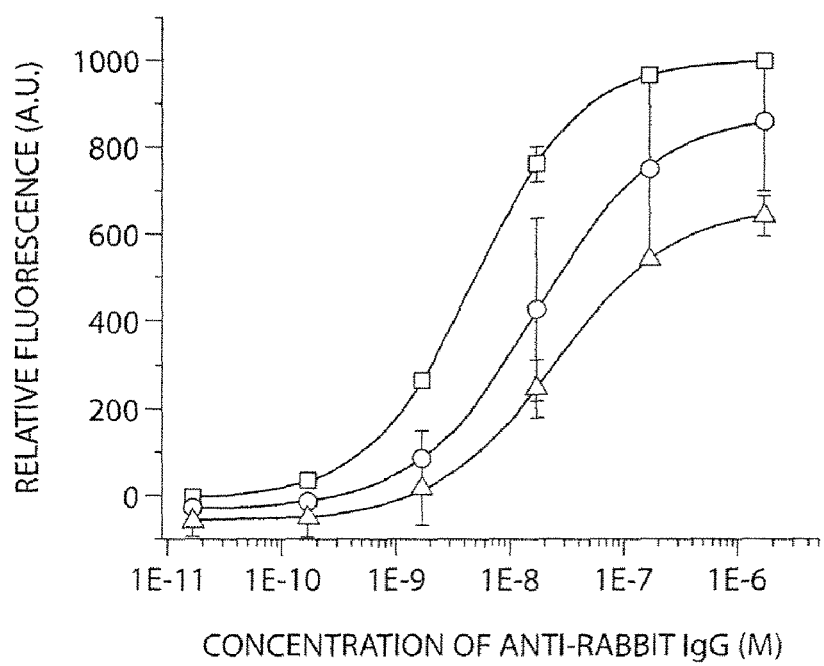
FIG. 22 illustrates an embodiment showing a change in response that varies with a change in antibody concentration.

Data are presented in FIG. 22 and were compensated for daily variations, using the titration curve obtained for the 8-cm plugs as an internal standard. Each titration curve represents the average of three experimental curves, obtained with an interval of one day. A sigmoidal fit for the internal standard was calculated and the data were transformed for the sigmoidal fit with the relation $y=a \cdot x+b$. The value of the constant a and b were required to obtain a fit that is $y=0$ at the lowest and $y=1000$ at the highest concentration of anti-rabbit IgG. All experimental data were transformed using the relation $y=a \cdot x+b$ and the average of three data points was calculated. The data presented in FIG. 22 were compensated for daily variations, using a third microfluidic chip as an internal standard. The calibrator consisted of four parallel channels (50 mm long, 50 μm wide and 50 μm deep) filled with solution of 0.5, 1, 2 and 4 μM of fluorescein in 50 mM sodium carbonate buffer pH 9.55. For each daily set of measurement, a new calibrator was prepared from a new microfluidic chip and the appropriate solutions of fluorescein. The fluorescence intensity plot vs. fluorescein concentration resulted in a line, which was fitted by linear regression. Each fluorescence data point obtained for the immunoassay was individually treated with the result of the linear fit, by subtracting the value of the intercept and then by dividing with the slope.

Figure 13:
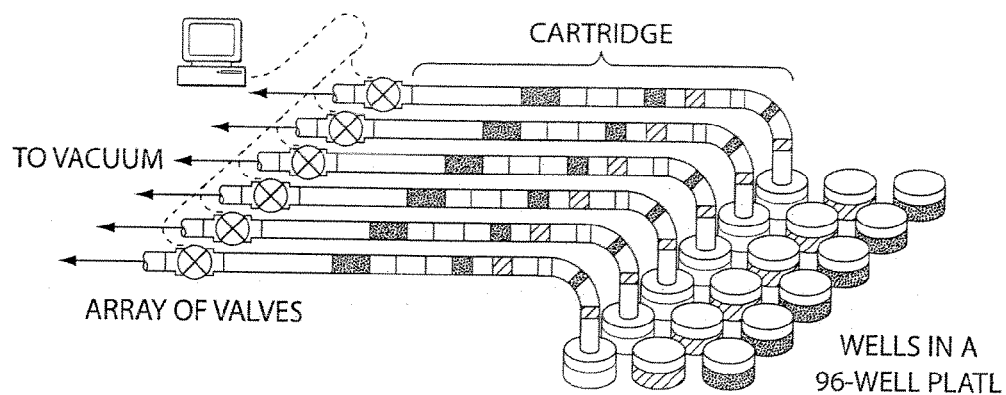
FIG. 13 illustrates a technique for filling a vessel.
Figure 14:
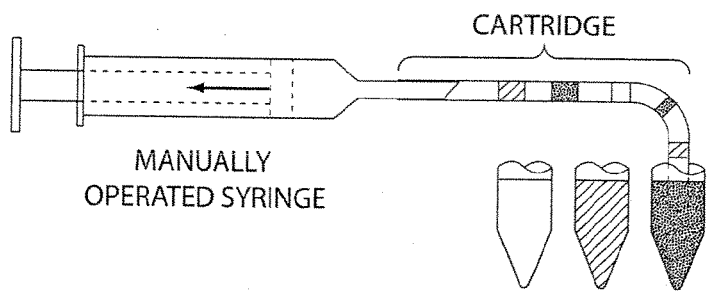
FIG. 14 illustrates another technique for filling a vessel.

Tubes, or cartridges, were prepared by cutting commercially available polyethylene (PE) tubing into 30-cm long units. The two methods investigated for filling the cartridge are illustrated in FIGS. 13 and 14. In the method depicted in FIG. 14 up to six PE cartridges were connected to an array of voltage-gated valves, which were in-turn connected to a −6 kPa vacuum source. Voltage pulses generated via a home-written Labview program operated the voltage-gated valves. Before initiating the reagent loading, the cartridges were filled with washing buffer (0.05% Tween® 20 in PBS) and the valves were activated to pump a 2-cm plug of air into the cartridges. The cartridges were then dipped in the appropriate liquid and a plug of liquid was aspirated into the cartridge by opening the valves. An opening time of 5 sec resulted in a 3-cm long plug or a volume of about 13.5 μL. Between each liquid plug, air was aspirated into the cartridge to separate physically each reagent and to avoid mixing of reagents in the cartridge. The valves and cartridges were affixed to a holder, which fits onto a 96-well plate, and the stock solutions of reagent were placed in the appropriate sequence into the wells. Using this system, plugs of reagents were filled accurately in six parallel cartridges with a precision of below ±14% in terms of plug length.

The second method, depicted in FIG. 14, used a manually operated Hamilton syringe connected at one end of a single length of PE tubing. This approach may be technically simpler than the method above, and may be more appropriate for the preparation of a limited number of cartridges. When the cartridge preparation was completed, the tubing end was heat-sealed, the cartridge was unplugged from the valve/syringe and the other end was heat-sealed. Cartridges containing as many as 10 plugs for a heterogeneous immunoassay were prepared.

Figure 16A:
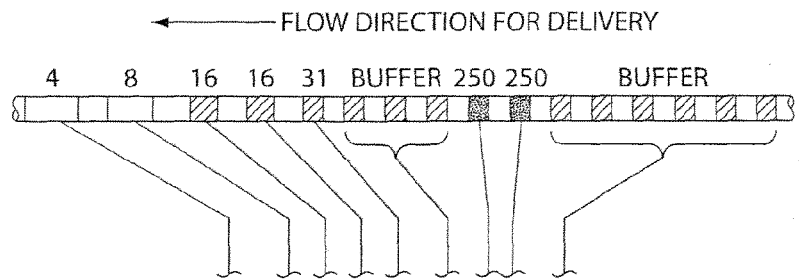
FIGS. 16a, b and c illustrate graphically the fluorescence response to a series of sequentially applied fluid plugs.
Figure 16B:
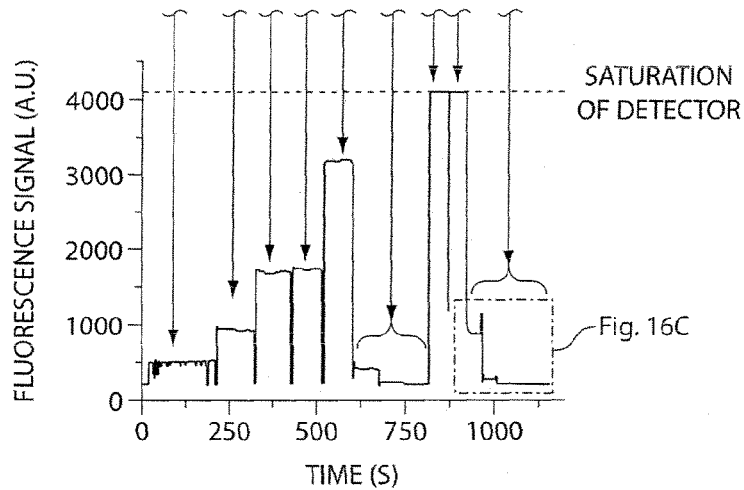
Figure 16C:
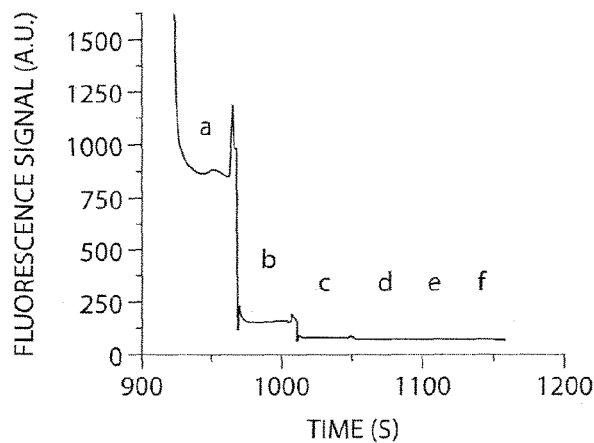

The air plugs located between each fluid plug ensured that no mixing between different reagents occurred in the cartridge. Using dyed plugs, it was observed that the plugs left small residues as they moved into the tubing. The trailing plugs were found to collect the residue. This process resulted in a plug-to-plug cross-contamination. Multiple, distinct plugs may be more effective at removing this residue. To quantify the cross-contamination and to determine how many rinsing plugs might reduce the residue to acceptable levels, a cartridge was filled with plugs of fluorescein dissolved in 50 mM carbonate buffer (pH 9.5) using the method depicted in FIG. 14. Plugs of fluorescein were loaded at various concentrations followed by one or more plugs of buffer. The cartridge was connected to the inlet of a 25-mm long, 50×50-μm microfluidic channel and the fluorescence intensity in the channel was recorded as the plugs were pumped through the microfluidic channel. Results are shown in FIGS. 16b and 16c. The detector showed a linear response for the dilution series of fluorescein, indicating that the data could be used for quantitative treatment. Quantification of the extent of plug-to-plug contamination trailing from a 31 μM fluorescein solution in three following buffer plugs showed (after background subtraction) a concentration by fluorescence of 7%, 0.9% and 0.1% relative to the 31 µM fluorescein plug. The cross-contamination from a plug of 250 µM fluorescein was measured. The presence of fluorescein in the six plugs following the 250 µM fluorescein solution was determined. While the signal of the 250 µM fluorescein plug saturated the detector, fluorescence was detected only in the first three plugs (to follow the fluorescein plug). These observations showed that three buffer plugs between each reagent plug were sufficient to prevent cross-contamination. Therefore, the introduction of three or more buffer plugs in the cartridge may serve a dual function: (i) preventing plug-to-plug contamination in the cartridge, and (ii) rinsing the substrate before the washing step, as may be desirable in applications such as micro-titer assays.

Figure 15:
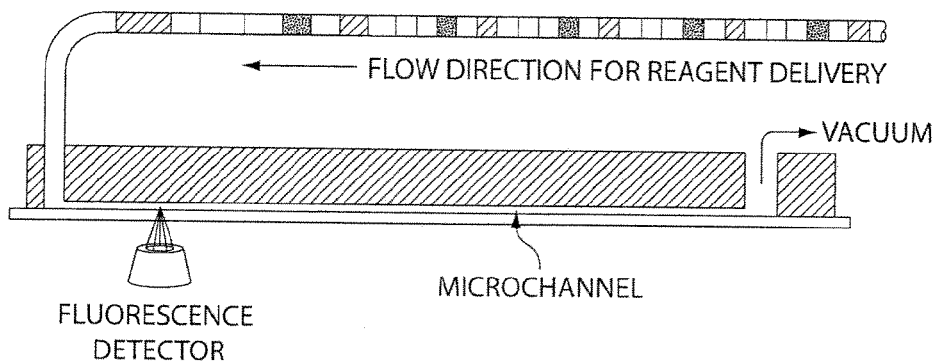
FIG. 15 illustrates one embodiment of delivering a series of fluids to an assay device.

In addition to air, perfluorodecalin (PFD) was evaluated as a separating fluid. The aqueous solutions wet the hydrophilic microchannels more than did PFD. When a PFD plug entered the microfluidic channel, it only partially flushed the aqueous solution out of the microchannel. The resulting incubation times and washing efficiency were thus irreproducible. Gaseous plugs travel through the microchannel more quickly than PFD plugs do at a given pressure differential. At ambient temperature, air has a viscosity of ~20 µPa·s, whereas the viscosity of PFD is ~5 mPa·s, or 250 times larger than that of air. Upon application of a pressure gradient, the volumetric flow rate through channel is inversely proportional to the viscosity of the fluid. A plug of air will therefore travel about 250 times faster than a plug of PFD. As illustrated in FIG. 15, air plugs in the cartridge have a similar length as do the reagent plugs. However, due to the fast transport of air, the detector read-out indicates that the time elapsed between two fluorescein plugs is less than 10 seconds. For comparison, a separation plug of similar length made of a liquid immiscible with water, such as PFD, took several minutes to travel through the microchannel. The total assay time may therefore be significantly reduced when gas-based separators are used instead of liquid-based separators between the reagent plugs.

Figure 17:
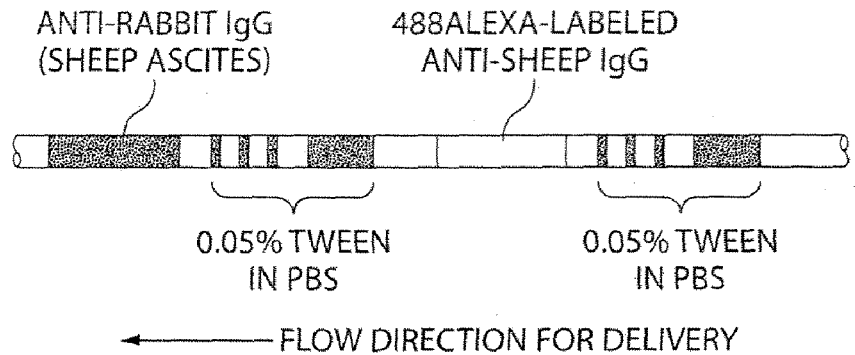
FIG. 17 provides a schematic illustration of various fluid reagent plugs in a vessel.
Figure 18:
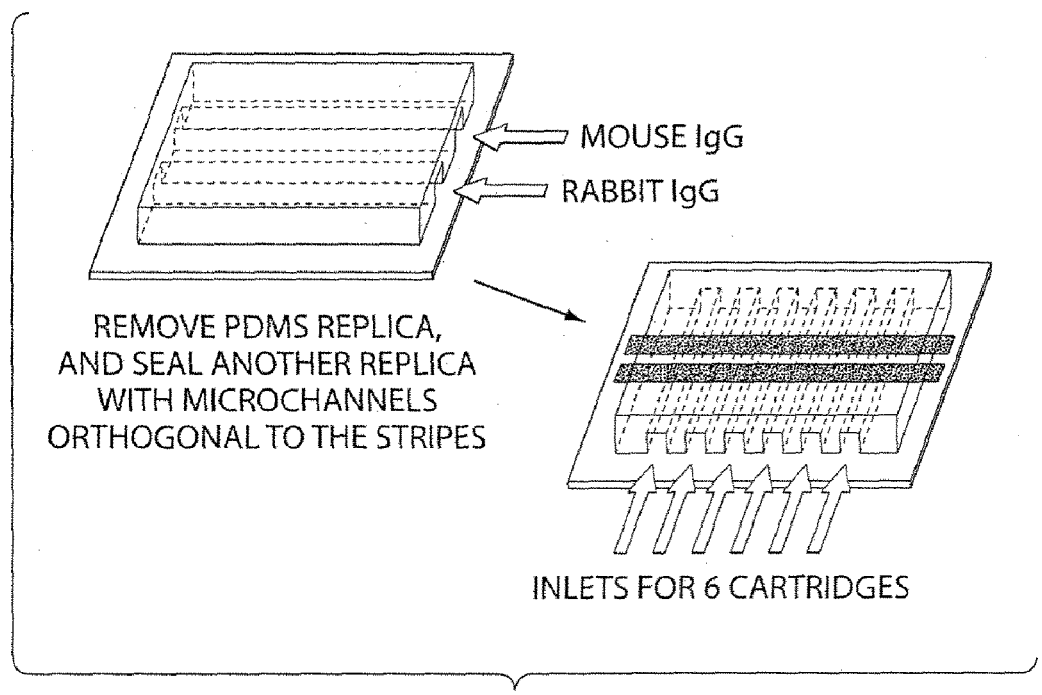
FIG. 18 illustrates a method for making a microfluidic assay device.
Figure 19:
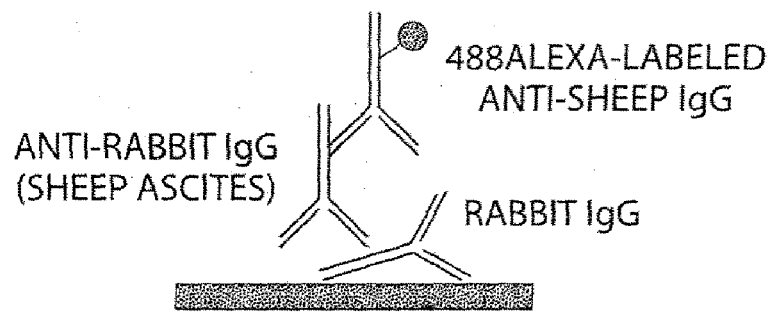
FIG. 19 provides a schematic illustration of associated components from the reagent fluids of the vessel of FIG. 17.
Figure 20:
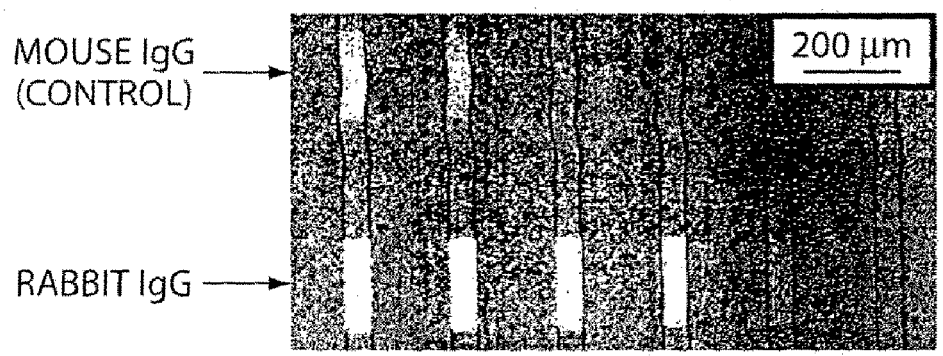
FIG. 20 is a photocopy of a fluorescent micrograph of an assay completed on the device of FIG. 18.

To illustrate the use of a cartridge for the sequential delivery of reagents, a microfluidic heterogeneous immunoassay for the detection of immunoglobulin G (IgG) raised against rabbit IgG (anti-rabbit) was performed. A cartridge was prepared as described above with a sequence of plugs containing sheep anti-rabbit IgG, 0.05% Tween in PBS, Alexa488-labeled donkey anti-sheep IgG and 0.05% Tween in PBS, with each antibody-containing plug followed by three plugs of 0.05% Tween in PBS (see FIG. 17). The heterogeneous immunoassay used was similar to others described herein and in co-pending U.S. Patent Application titled "Assay Device and Method,", filed on even date herewith and incorporated by reference in its entirety herein, filed one even date herewith. A PDMS replica was sealed onto an unstructured polystyrene substrate. Two parallel microchannels were filled, one with a solution of rabbit IgG and the other with a solution of mouse IgG. After incubation, the PDMS slab was removed to reveal the bands of rabbit IgG and mouse IgG physisorbed on polystyrene substrate. To perform the immunoassay, a second PDMS slab with six microfluidic channels was placed orthogonal to stripes of antigen (see FIG. 18) and the surface of the polystyrene in the microchannel was blocked with 0.05% Tween 20 in PBS. The cartridge was connected to the microchannel inlet and a −15 kPa vacuum was applied at the outlet using a hand-operated vacuum pump. The reagents were sequentially delivered to the microfluidic platform. Observation in the microchannel by fluorescence microscopy revealed a clear fluorescence signal originating from the fluorescent immunocomplex built on the rabbit IgG stripe (see FIG. 20), and no fluorescence was detected outside the mouse IgG stripe. Some non-specific binding was observed on the surface of mouse IgG when samples with high concentration of protein were used. The total assay time to perform the immunoassay could be adjusted to between 2 and 8 minutes, depending on the length of the plugs in the cartridge (see below).

Figure 21:
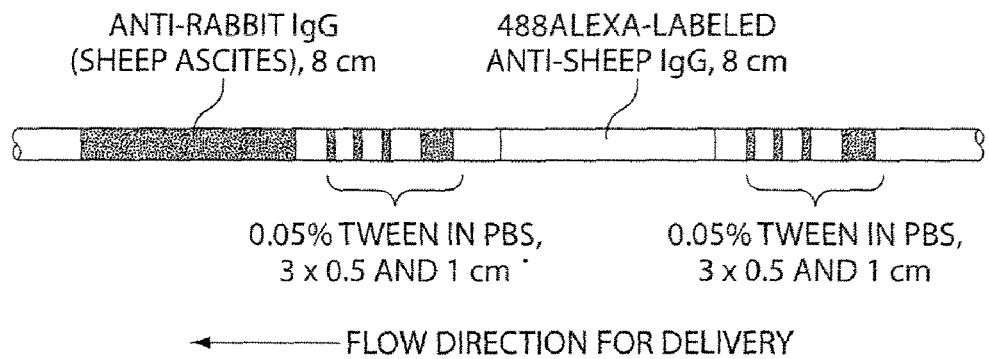
FIG. 21 provides another illustration of various fluid reagent plugs in a vessel.

The dynamic range of the heterogeneous immunoassay of anti-rabbit IgG was determined by performing the assay with a series of 10-fold dilutions of anti-rabbit IgG in the cartridges. The incubation time of the sample has a direct influence on of the performance of the assay. The dynamic range achieved using the technique described above was determined by recording the signal as a function of the incubation time. Since the length of the plug may be directly proportional to the incubation time, cartridges were prepared, where the length of the antibody-containing plugs was varied from 2 to 4 and 8 cm. In the cartridges, both antibody-containing plugs were followed by three rinsing plugs (0.5 cm, 2.3 µL) and one washing plug (1 cm, 4.5 µL) containing 0.05% Tween in PBS (see FIG. 21). The specific incubation times for the antibody-containing plug and the total assay time are given in Table 2, below. The maximum signal increased when longer incubation times were used, and the dynamic range when using 8-cm long plugs was displaced by about one order of magnitude toward the low sample concentrations compared to the assay with 2-cm long plugs.

TABLE 2

Plug length in cartridges and corresponding assay time

| Plug length[§] | Plug volume[§] | Plug delivery time[§] | Total assay time |
|---|---|---|---|
| 2 cm | 9 µL | 30 s | 2' 00" |
| 4 cm | 18 µL | 67 s | 3' 50" |
| 8 cm | 36 µL | 130 s | 7' 45" |

Figure 23:
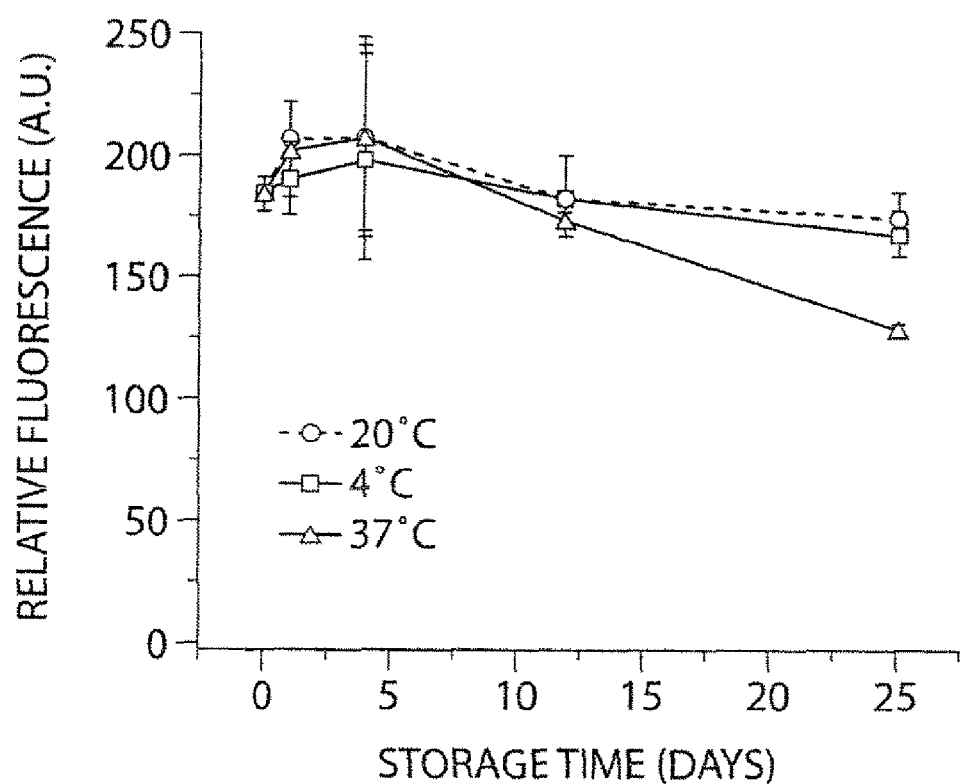
FIG. 23 illustrates graphically a change in fluorescence against cartridge storage time.

A cartridge may serve as long-term storage for reagents before an assay is performed. The long-term stability of the reagents in the cartridges was evaluated, by preparing about 70 cartridges loaded with a sample of 167 nM anti-rabbit IgG and using them over the course of 12 days. The antibody-containing plugs were 8 cm-long. Immediately after the cartridge preparation, the assay was performed on two parallel chips with 6 cartridges and the fluorescence signal arising from the immunocomplex was recorded. The remaining cartridges were split into three batches, each stored at a different temperature: 4° C., room temperature, and 37° C. Later, the immunoassay was repeated on two freshly prepared chips with four cartridges from each batch. The system illustrated in FIG. 18 can accommodate up to six cartridges in parallel. Two cartridges from all batches were used on each chip, and the average fluorescence signal as a function of the time of storage was plotted (see FIG. 23). A slight decrease in signal was observed (see the solid line in FIG. 23, representing the average fluorescence intensity recorded for all 12-data points). On a given chip, small variations (i.e. typically less than 5%) were observed between the signals obtained from the cartridges stored at different temperatures. However, the chip-to-chip variations were larger (sometimes as high as 25%) than the cartridge-to-cartridge variations on the same chip. This suggests that the procedure for the preparation of the microfluidic platform may be the source of the reduced reproducibility of the immunoassay results. A comparison of the signal obtained with cartridges stored at different temperatures but used on the same chip can, however, reliably assess the loss of signal associated with the storage conditions. From the graphics illustrated in FIG. 23, it was found that the cartridges can be stored at temperatures as high as 37° C. for two weeks without significant loss of activity compared to those stored at 4° C. or 20° C. After four weeks, the cartridges stored at 37° C. showed a decrease in activity compared to those stored at 4° C. or 20° C. The overall activity of the immunoreagents in cartridges stored at 20° C. remained essentially unchanged for extended period of times. This was determined by comparing the titration curves obtained for anti-rabbit IgG using freshly prepared cartridges and cartridges stored for 4 weeks at 20° C., 37° C. and 4° C.

To compare a method of the invention with existing methods, an experiment was designed to assay HIV antibodies using the present method as well as ELISA techniques employing chemiluminescence, fluorescence and absorbance. Procedures and results are described below.

Reagents and equipment were obtained as follows. Rabbit IgG, anti-rabbit IgG (horseradish peroxidase conjugated), anti-rabbit IgG (alkaline phosphatase conjugated), anti-rabbit IgG (gold conjugated), p-nitrophenylphosphate (pNPP), and the silver enhancement kit were obtained from Sigma-Aldrich (St. Louis, Mo.). AttoPhos was purchased from Promega Corp. (Milwaukee Wis.). SuperSignal ELISA Femto Max was purchased from Pierce (Rockford, Ill.). BluePhos phosphatase substrate was purchased from KPL (Gaithersburg, Md.). HIV Env antigen (gp41) was purchased from Research Diagnostics (Flanders, N.J.). HIV positive serum and control serum were purchased from Golden West Biologicals Inc. (Temecula, Calif.).

Immunoassays in 96-well microtiter plates were performed using a Tecan Genesis liquid handling robot (Center for Genomics Research, Harvard University). The following Nunc MaxiSorp polystyrene plates were used for the silver reduction and ELISA assays: clear plates for silver reduction and absorbance, black plates for fluorescence and white plates for chemiluminescence. Rabbit IgG (70 µL for each well) in ten-fold dilutions (10 µg/mL to 100 µg/mL, which corresponded to 67 nM to 670 fM) was added to the microwells, except for one row to which PBS was added as a negative control; incubation time was 2 hours. Blocking buffer (100 µL of 0.05% Tween-20 and 1% BSA in PBS) was then added, and left to incubate for 30 minutes. For secondary antibodies, dilutions (30 µL of 0.05% Tween-20 in PBS) of 1:300 anti-rabbit IgG (gold-conjugated), 1:1000 anti-rabbit IgG (alkaline phosphatase), and 1:1000 anti-rabbit IgG (horseradish peroxidase) were used; incubation time was 1 hour. For ELISA substrates, pNPP (100 uL; 3 minute incubation), AttoPhos (100 uL, used within 1 week of opening; 10 minute incubation), and SuperSignal Femto ELISA (100 uL; after 5 minutes). For silver enhancement, the solutions of silver and initiator (at 4° C.) were mixed in a 1:1 ratio immediately before development; it was filtered through a 0.2 µm filter, and 100 uL was added to each well. After a 20 minute incubation, the silver enhancer solution was removed, and each well was washed with water. In general, warming the silver enhancement solution from 4° C. to room temperature increased the rate of silver deposition. In between the addition of each new reagent, each well was washed three times with PBS, with the following exception: deionized water was used to wash the wells after incubation with anti-rabbit IgG (gold) and before silver enhancement, in order to avoid precipitation of AgCl. The plate readers used were Spectramax Plus 384 for absorbance measurements, and Spectramax Gemini XS for fluorescence and chemiluminescence measurements.

The output of the optical IC was light transmittance; apparent absorbance values were calculated using the relation $A=-\log(T/T_0)$, where A is the absorbance, and T and $T_0$ are the transmission of the light through the sample and reference, respectively, to the photodetector. Air was used as the reference in the plate reader, and a blank polystyrene plate was used as the reference for the portable detector.

Figure 7:
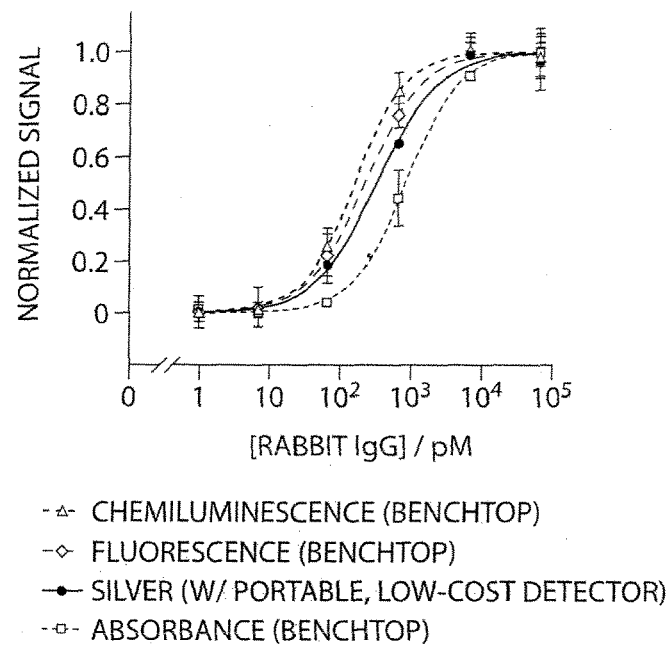
FIG. 7 provides graphical data regarding four different assay techniques.

The absorbance, fluorescence, and chemiluminescence readings (y) were fit to sigmoidal curves using the software Kaleidagraph and the following equation: $y=Ax^n/(B+x^n)+C$, where x is the concentration of the analyte, and A, B, C and n are floating parameters. Results are illustrated in FIG. 7. This equation describes a general sigmoidal curve with the lowest possible number of floating parameters (four). Curve fitting to all four titrations gave correlation coefficients of over 0.99. The readings y for all four titrations were normalized to the same scale (0 to 1) by linearly transforming each data set to achieve the values of A=1 (asymptote as x approaches infinity) and C=0 (y-intercept).

Limits of detection were calculated according to the IUPAC definition: three times the standard deviation of the blank sample ("noise") divided by the slope ("sensitivity"). In samples with no rabbit IgG (i.e. negative controls), the methods that exhibited the least to most noise were (after normalization of the signal from 0 to 1): 0.006 for absorbance of pNPP, 0.014 for chemluminescence of SuperSignal ELISA Femto Max, 0.023 for silver (using the portable detector), and 0.066 for fluorescence of AttoPhos. The methods that showed the highest to lowest sensitivities, which were measured as slopes of the best-fit curves in the middle of the linear working range of detection (signal of 0.50), were (in normalized units per 100 pM of analyte): 0.193 for chemiluminescence, 0.121 for fluorescence, 0.078 for silver, and 0.035 for absorbance.

Figure 8:
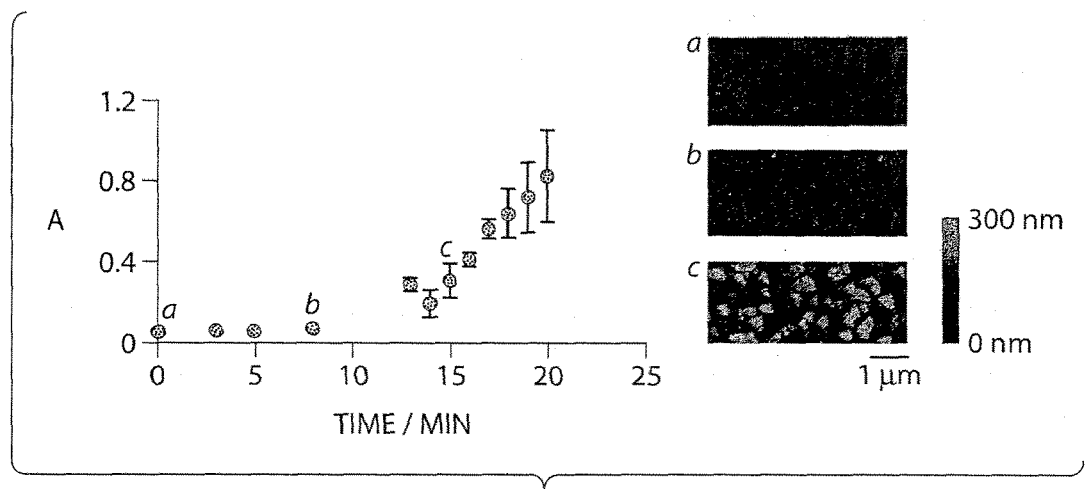
FIG. 8 provides graphical data indicating absorbance vs. time of exposure and provides photocopies of micrographs showing an opaque material.

To prepare immunoassay samples for analysis by AFM, holes (4 mm in diameter) were punched in a PDMS slab, and the PDMS slab was placed onto a polystyrene surface. Immunoassays were carried out in individual PDMS wells. After silver development, the PDMS slab was removed, and the samples on the flat polystyrene substrate were analyzed by tapping mode AFM. AFM was performed with a Dimension 3100 Scanning Probe Microscope (Digital Instruments, Santa Barbara, Calif.) in tapping mode, using silicon probes (Si #MPP-111000; NanoDevices, Santa Barbara, Calif.) at a scan rate of 0.35 Hz. AFM micrographs are provided in FIG. 8. Streaking was observed for samples with the largest silver grains, which suggested that the silver grains were loosely bound to the surface.

The microfluidic device was fabricated in PDMS using published procedures in soft lithography. The dimensions of the microchannels were 2 mm in width and 130 µm in height. The polystyrene surface was initially patterned with a stripe of HIV Env antigen (10 µg/mL) by filling a PDMS channel (conformally sealed onto the polystyrene plate) with the antigen solution. After an overnight incubation, the channel was emptied, the PDMS slab removed from the polystyrene surface, and rinsed the surface with deionized water. The stripe of antigen was covered with an unstructured slab of PDMS, and oxidized the remaining surface of polystyrene with oxygen plasma. After removal of the plasma-protective PDMS slab, another microfluidic channel (also freshly plasma-oxidized) was sealed orthogonally to the antigen stripe. The dimensions of these microchannels were 2 mm in width and 40 µm in height; the width of the channel must be large enough to register a signal with the portable detector. To avoid sagging of the PDMS, pillars (which took up 12% of the surface area) were included in the channel design. The anti-HIV antibody assay was carried out in the microfluidic channels with the following incubation times: 1 to 4 hours for blocking, 10 minutes for samples, 10 minutes for gold-labelled anti-human IgG, and 13.5 minutes for silver enhancement solution. After 6.5 minutes of silver enhancement, the silver solution was exchanged with a freshly prepared one. The PDMS microchannel was removed above the initial stripe of antigen before measuring the optical density of the silver film. The HIV assay in microwells were performed with the following incubation times: overnight for HIV Env antigen, 2 hours for blocking, 3 hours for samples, 1 hour for gold-labelled anti-human IgG, and 10 minutes for silver enhancement solution.

For each concentration of rabbit IgG and each dilution of human serum, triplicates of the immunoassay were performed, and average values and standard deviations were calculated.

The electronic circuit consisted of a transmitter section and a receiver section. In the transmitter section, a 1 kHz oscillator modulated the light output of a laser diode. A red semiconductor laser diode (Sharp GH06510B2A; normally used for optical data storage applications such as DVD) was used; it emitted at a wavelength of 654 nm with a maximum power of 10 mW. The laser output went through the sample to the receiver section. An optical IC (Sharp IS455; normally used in photocopy machines) to detect and amplify the signal. IS455 provided a linear output current with respect to the input illuminance (1 µA per lux). (The dimensions and costs of the red laser diode and the optical IC were 5.6 mm and $10, and 5.0 mm and $2, respectively.) The signal was then filtered by a second-order bandpass filter centered at 1 kHz, and its amplitude registered by a peak detector. The output of the peak detector was connected to an Analog/Digital converter that also encoded the output into binary coded decimal (Intersil ICL7106). The signal was displayed by a 3.5 digit liquid crystal display, which provided an output readout range from 0 to 1999. The entire circuitry was operated with either a 9 V battery or a single polarity 5 V source, which was inverted with a CMOS voltage converter (Intersil ICL7660) to create a ±5 V supply. To reduce the noise in the system, pulse modulation of the optical signal at 1 kHz was used to filter the noise power in the frequency spectrum; as a result, only the portion of the optical noise that fit in the pass band of the receiver filter contributed to the overall noise detected. The system could also be used without the signal modulation (i.e. at direct current)

The laser diode and optical IC were placed on two separate circuit boards that were held at a fixed orientation to ensure consistent alignment of the light path from the light source to the photodetector. Between the light source and photodetector, a glass plate was placed. A black transparency, with a pinhole aligned with the light path, was placed on the glass plate to block the transmission of stray light that did not enter the sample. To record a measurement, a polystyrene plate (either a 96-well plate or a plate with a microfluidic device) was placed onto the glass plate. The sample was aligned to the light path by roughly placing the sample over the pinhole, and finely adjusting the x and y position of the polystyrene plate until a maximum transmittance was achieved. The reading from the liquid crystal display was recorded.

To compare two detection methods independent of analyte, microwells of a 96 well plate were subjected to readings by an IC and by a commercial plate reader.

Absorbance of microwells containing different concentrations of BluePhos, which absorbs maximally at 600 nm, as measured by a UV-visible absorbance plate reader and the optical IC described in this study. A direct ELISA was performed on 0.67 pM to 0.67 nM of rabbit IgG as the analyte, using an anti-rabbit IgG conjugated to alkaline phosphatase and BluePhos as the phosphatase substrate. Results are provided in FIG. 10 and FIG. 11. Measurements with both devices were made at 654 nm. The best fit line by linear regression is shown (correlation coefficient of 0.998, slope of 1.01, y-intercept of 0.08). Error bars are standard deviations of measurements of three different microwells.

In this assay, in which the colorimetric product is a homogeneous solution in the microwell, the two detection methods resulted in almost perfect agreement (correlation coefficient of 0.998). Thus, inhomogeneity of silver deposition on the surface may have contributed to the imperfect agreement between the two measurement methods, such that different parts of the same well were sampled by the laser diode and by the plate reader (correlation coefficient of 0.996).

Example 2

A schematic representation of one embodiment and an optical detection device is provided in FIG. 9. (A) Red light from the laser diode passes through the silver-coated microwell containing the sample to the optical IC. A pinhole was used to block stray light that did not pass through the sample. The laser diode and the optical IC were driven by the same circuit, which also had an integrated liquid crystal display that showed the measured transmittance value.

Example 3

Figure 10:
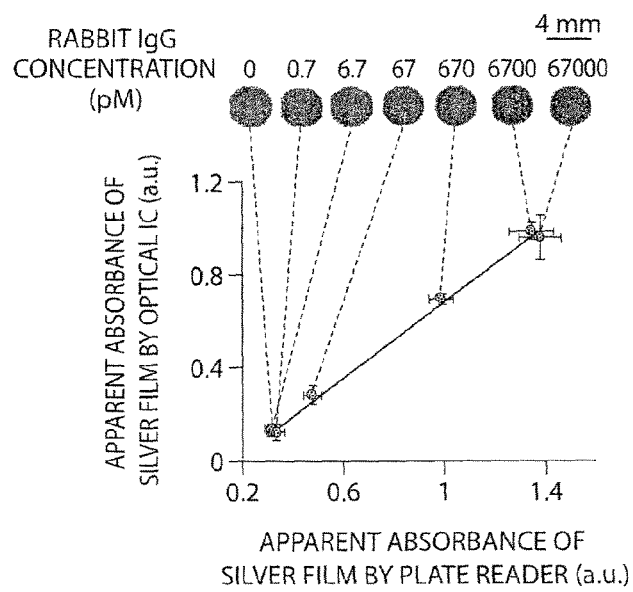
FIG. 10 provides graphical data comparing apparent absorbance by two different techniques.
Figure 11:
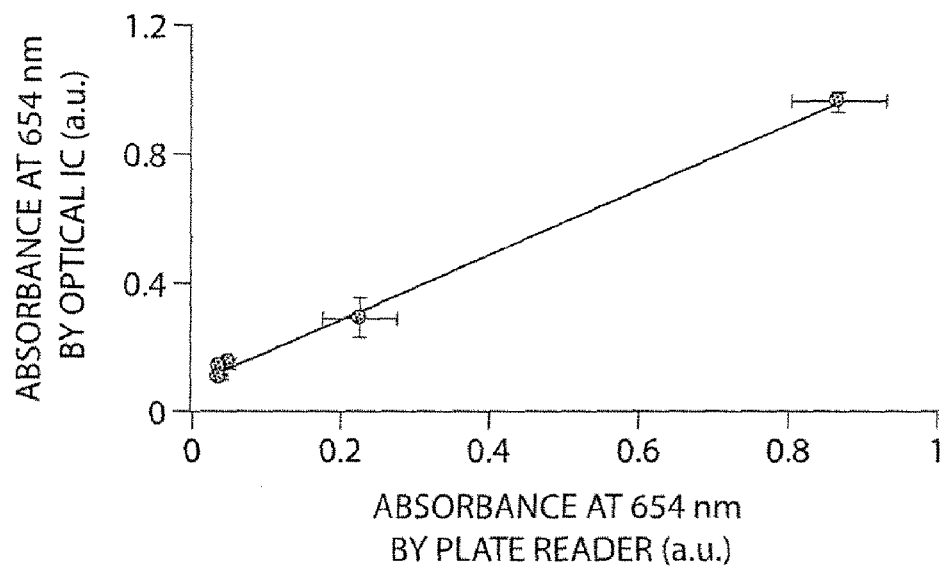
FIG. 11 provides additional graphical data comparing absorbance by two different techniques.

FIG. 10 provides a comparison of readings of an immunoassay using an optical IC and a UV-visible plate reader. An immunoassay using silver reduction was performed on a 96-well plate that detected rabbit IgG. Optical micrographs of the silver films on microwells are shown for each sample. The apparent absorbance of each microwell was measured by an optical IC, and compared to its reading by a UV-visible plate reader; both measurements were made at 654 nm. The best-fit line by linear regression has a correlation coefficient of 0.989, slope of 1.12, and y-intercept of 0.16.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method comprising:
providing a first and a second fluid maintained separately from each other by a third fluid in a common, sealed vessel, wherein the third fluid is adjacent to and substantially immiscible with the first and second fluids;
unsealing the vessel;
transferring the first, third and second fluids in series from the vessel to a reaction site; and
avoiding substantial contact between the first and second fluids, at least until after the fluids have been applied to the reaction site.

2. A method comprising:
unsealing a sealed vessel containing a first and a second fluid maintained separately from each other by a third fluid adjacent to and substantially immiscible with the first and second fluids;
applying in series the first, third, and second fluids to a reaction site, wherein the vessel and the reaction site are formed in a microfluidic chip; and
avoiding substantial contact between the first and second fluids, at least until after the fluids have been applied to the reaction site.

3. A method comprising:
unsealing a sealed vessel containing a first and a second fluid maintained separately from each other by a third fluid adjacent to and substantially immiscible with the first and second fluids;
applying in series the first, third, and second fluids to a reaction site, wherein the vessel and the reaction site are integrally connected to one another; and
avoiding substantial contact between the first and second fluids, at least until after the fluids have been applied to the reaction site.

4. The method of claim 1 further comprising connecting the vessel to a device comprising the reaction site.

5. The method of claim 1 wherein the vessel and reaction site are on a common platform.

6. The method of claim 1 wherein the vessel and reaction site are integrally connected during storage of the first, second and third fluids in the vessel.

7. The method of claim 1 wherein the vessel comprises a tube.

8. The method of claim 1 further comprising applying a pressure differential across the reaction site.

9. The method of claim 8 wherein the pressure differential is provided by suction on a downstream side of the reaction site.

10. The method of claim 8 wherein the pressure differential is provided by a pump on an upstream side of the reaction site.

11. The method of claim 1 wherein the first and second fluids are transferred in series to the reaction site without actuating a valve.

12. The method of claim 1 wherein the first and second fluids are transferred in series to the reaction site without actuation of any device that controls the rate, the order, or timing of introduction of either of the first and second fluids, relative to each other, to the reaction site.

13. The method of claim 4 wherein the device is a microfluidic device.

14. The method of claim 1 wherein at least one of an antibody or an antigen is associated with the reaction site.

15. The method of claim 1 wherein the third fluid is a gas or a gaseous mixture.

16. The method of claim 1 wherein the first fluid and/or second fluid is a rinse solution.

17. The method of claim 4 further comprising disposing a sample in the device prior to applying the first and second fluids to the reaction site.

18. The method of claim 1 wherein the vessel contains a fourth fluid, the method further comprising combining the fourth fluid and the second fluid while transferring the first, third, and second fluids from the vessel to the reaction site.

19. The method of claim 1 wherein the vessel has a length to inner diameter ratio of at least 10:1.

20. The method of claim 1 wherein the vessel has an inner diameter of less than 1 millimeter.

21. The method of claim 1 wherein the vessel has an inner diameter of less than 500 microns.

22. The method of claim 1 wherein one of the fluids comprises a gold conjugated antibody.

23. The method of claim 1 wherein one of the fluids comprises a metal precursor.

24. The method of claim 23 further comprising electrolessly depositing metal at the reaction site to produce an opaque material.

25. The method of claim 24 further comprising determining light absorbance or transmission through the opaque material.

26. The method of claim 1, wherein the first and second fluids are maintained separately from each other by the third fluid in the common, sealed vessel for greater than one hour.

27. The method of claim 2 wherein at least one of an antibody or an antigen is associated with the reaction site.

28. The method of claim 2 wherein the third fluid is a gas or a gaseous mixture.

29. The method of claim 2 wherein the first fluid and/or second fluid is a rinse solution.

30. The method of claim 2 further comprising disposing a sample in the microfluidic chip prior to applying the first and second fluids to the reaction site.

31. The method of claim 2 wherein the vessel has a length to inner diameter ratio of at least 10:1.

32. The method of claim 2 wherein the vessel has an inner diameter of less than 500 microns.

33. The method of claim 2 further comprising electrolessly depositing metal at the reaction site to produce an opaque material.

34. The method of claim 33 further comprising determining light absorbance or transmission through the opaque material.

35. The method of claim 2 wherein the vessel contains a fourth fluid, the method further comprising combining the fourth fluid and the second fluid while transferring the first, third, and second fluids from the vessel to the reaction site.

36. The method of claim 33 wherein at least one of the first, third, and second fluids comprises a metal precursor.

37. The method of claim 2 wherein the reaction site is adapted for allowing a binding event to occur between at least two binding partners, and wherein at least one of the binding partners comprises an antibody.

38. The method of claim 1 wherein the reaction site is adapted for allowing a binding event to occur between at least two binding partners, and wherein at least one of the binding partners comprises an antibody.

39. The method of claim 3 wherein the third fluid is a gas or a gaseous mixture.

40. The method of claim 39 wherein the first fluid and/or second fluid is a rinse solution.

41. The method of claim 3 wherein the vessel has a length to inner diameter ratio of at least 10:1.

42. The method of claim 41 wherein the vessel has an inner diameter of less than 500 microns.

43. The method of claim 3 wherein at least one of the first, third, and second fluids comprises a metal precursor.

44. The method of claim 43 further comprising electrolessly depositing metal at the reaction site to produce an opaque material.

45. The method of claim 44 further comprising determining light absorbance or transmission through the opaque material.

46. The method of claim 39 wherein the vessel contains a fourth fluid, the method further comprising combining the fourth fluid and the second fluid while transferring the first, third, and second fluids from the vessel to the reaction site.

47. The method of claim 3 wherein the reaction site is adapted for allowing a binding event to occur between at least two binding partners, and wherein at least one of the binding partners comprises an antibody.

48. The method of claim 18 wherein the fourth fluid is stored in the vessel prior to the unsealing step.

* * * * *